(12) United States Patent
Wengreen

(10) Patent No.: US 8,136,431 B2
(45) Date of Patent: Mar. 20, 2012

(54) TORQUE WRENCH FOR IMPLANTABLE MEDICAL DEVICES

(75) Inventor: Eric John Wengreen, Stanford, CA (US)

(73) Assignee: Medtronic, Inc., Minneapolis, MN (US)

( * ) Notice: Subject to any disclaimer, the term of this patent is extended or adjusted under 35 U.S.C. 154(b) by 413 days.

(21) Appl. No.: 12/533,995

(22) Filed: Jul. 31, 2009

(65) Prior Publication Data

US 2010/0275746 A1  Nov. 4, 2010

Related U.S. Application Data

(60) Provisional application No. 61/174,455, filed on Apr. 30, 2009.

(51) Int. Cl.
*B25B 23/14* (2006.01)
*B25B 23/143* (2006.01)

(52) U.S. Cl. .......................................... 81/477; 81/467

(58) Field of Classification Search ................ 81/429, 81/467, 473–477, 480, 481
See application file for complete search history.

(56) References Cited

U.S. PATENT DOCUMENTS

| | | | | |
|---|---|---|---|---|
| 2,461,447 A * | 2/1949 | Siesel | ............................. | 464/37 |
| 5,224,403 A * | 7/1993 | Rueb | .............................. | 81/477 |
| 5,368,480 A * | 11/1994 | Balfour et al. | ................ | 433/141 |
| 5,779,409 A * | 7/1998 | Manzolli | ............................ | 411/7 |
| 5,996,453 A * | 12/1999 | Blacklock | ....................... | 81/467 |
| 6,439,086 B1 * | 8/2002 | Bahr | .............................. | 81/467 |
| 6,499,358 B1 * | 12/2002 | Hogan et al. | ............... | 73/862.21 |
| 7,159,494 B2 * | 1/2007 | Jamnia et al. | ................... | 81/467 |
| 7,824,428 B2 * | 11/2010 | Mikkonen et al. | ............ | 606/270 |
| 2007/0274800 A1 * | 11/2007 | Mikkonen et al. | ............. | 411/15 |
| 2009/0218813 A1 * | 9/2009 | Helstern | ...................... | 285/355 |

* cited by examiner

*Primary Examiner* — David B Thomas
(74) *Attorney, Agent, or Firm* — Carol F. Barry

(57) ABSTRACT

A torque wrench for implantable medical devices is disclosed. The torque wrench comprises a first and a second component. The first component has first and second ends with a bore extending between the first and second ends of the first component. The first component includes a plurality of anti-rotation members extending from an inner surface of the bore at the second end of the first component. A second component includes a middle portion having a first and second ends. A drive shaft extends from the first end and a plurality of fingers extends from an exterior surface of the second end. The second component is received in the bore of the first component such that the fingers are interdigitate with the anti-rotation members.

16 Claims, 52 Drawing Sheets

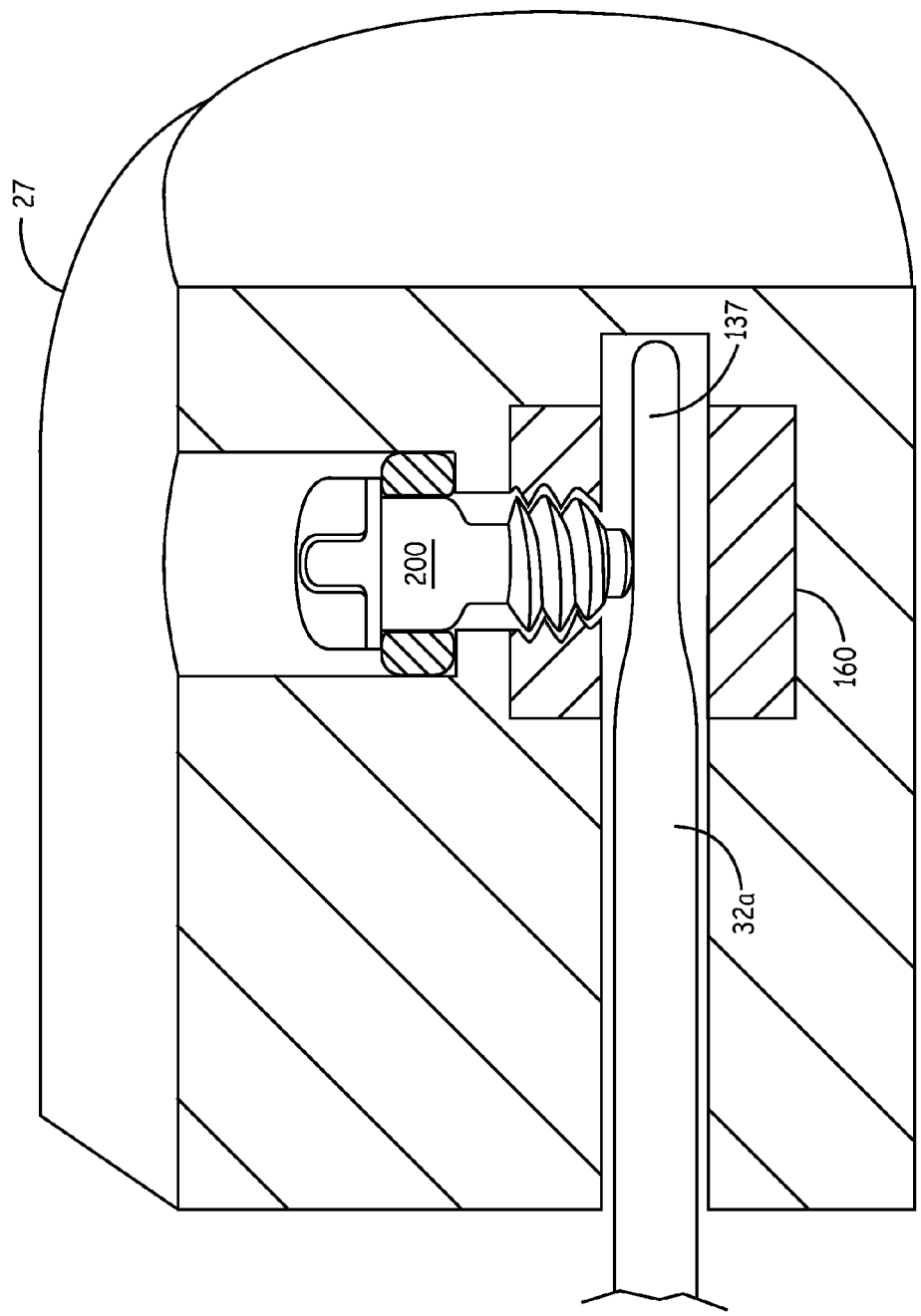

TORQUE WRENCH FOR IMPLANTABLE MEDICAL DEVICES

CROSS-REFERENCE TO RELATED APPLICATIONS

This application claims the benefit of U.S. Provisional Application No. 61/174,455, filed on Apr. 30, 2009. The disclosure of the above application is incorporated herein by reference.

TECHNICAL FIELD

The present disclosure relates generally to wrenches, and, more particularly, to torque wrenches used to rotate a connector in an implantable medical device.

BACKGROUND

Many implantable medical devices such as pacemakers, defibrillators and neural stimulators can sense various physiological parameters through medical leads and/or deliver therapy to tissue. Leads include an elongated flexible lead body. The lead body comprises one or more insulated elongated conductors with one or more electrodes disposed at a distal end of the conductors.

To ensure the lead is properly secured to an implantable medical device, the proximal end of the conductor, referred to as a terminal pin, is passed through a conductor bore in the connector block of a header. A setscrew, which passes through a threaded setscrew bore that intersects with the lead bore, is positioned to contact the conductor. A very small surgical torque wrench is then used to apply a certain amount of torque to the setscrew. Torque applied to the setscrew should provide a retention force between the setscrew and the conductor that is sufficiently large to prevent the conductor from dislodging from the header yet low enough to prevent the torque from damaging the setscrew or conductor. After the setscrew has been tightened, the torque wrench is typically discarded to ensure contaminants from one surgical procedure are not transferred to another procedure. It is desirable to develop surgical torque wrenches that apply appropriate torque to a setscrew when securing a lead to a header and that are also inexpensive in order to reduce the cost of such procedures to patients.

BRIEF DESCRIPTION OF THE DRAWINGS

The following description of the preferred embodiments is merely exemplary in nature and is in no way intended to limit the invention, its application, or uses. For purposes of clarity, the same or similar reference numbers are used in the drawings to identify similar elements.

FIG. 3 shows a schematic cutaway view of the header of FIG. 1 taken along lines 3-3;

DETAILED DESCRIPTION

Figure 1:
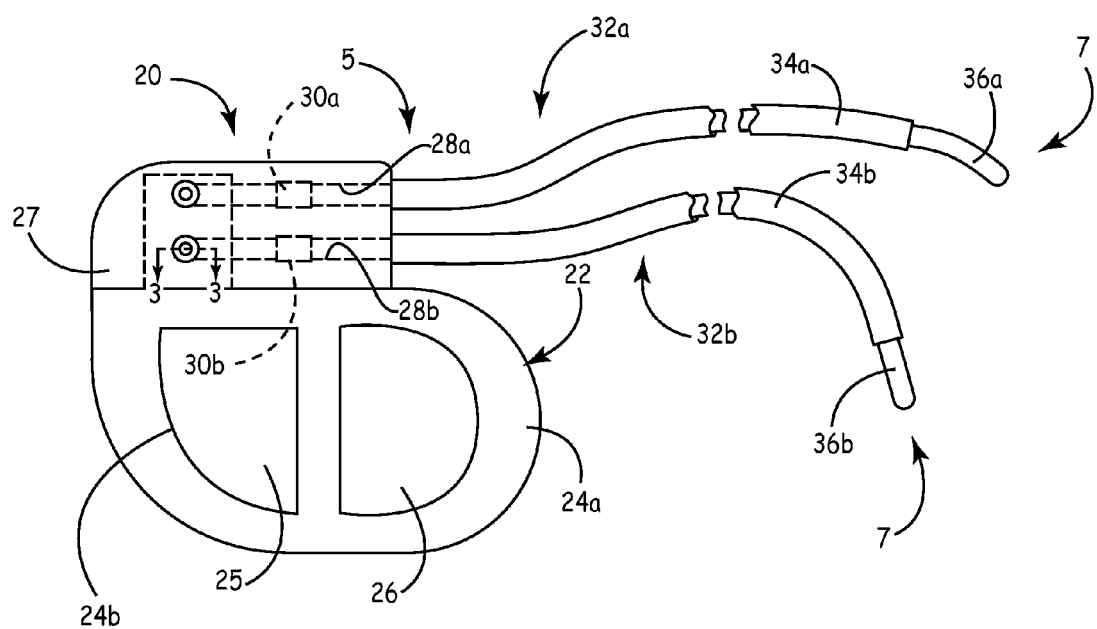
FIG. 1 illustrates an exemplary implantable medical device system that has leads.

The following description of the preferred embodiments is merely exemplary in nature and is in no way intended to limit the invention, its application, or uses. For purposes of clarity, similar reference numbers are used in the drawings to identify similar elements.

The present disclosure relates to a surgical torque wrench. A surgical torque wrench can be used to securely connect a medical electrical lead to an implantable medical device. One or more embodiments of the torque wrench consist solely of a first component and a second component. By forming a torque wrench with two components instead of, for example, nine or more components as that which is used with conventional torque wrenches for IMDs, the torque wrench of the present disclosure is easier to manufacture, assemble and potentially use. Additionally, a lower cost can be realized by patients who undergo surgery using the torque wrench described herein.

In one or more embodiments, a surgical torque wrench includes a first component that has first and second ends and a bore extending between the first and second ends. At the second end of the first component, a plurality of anti-rotation members extend from an inner surface of the bore. The second component includes a middle portion having a first and second ends. A drive shaft extends from the first end while a plurality of fingers extend from an exterior surface of the second component. The second component is received in the bore of the first component, such that the drive shaft partially extends outside the first end of the first component and the plurality of fingers are interdigitate with the anti-rotation members of the first component.

Figure 2:
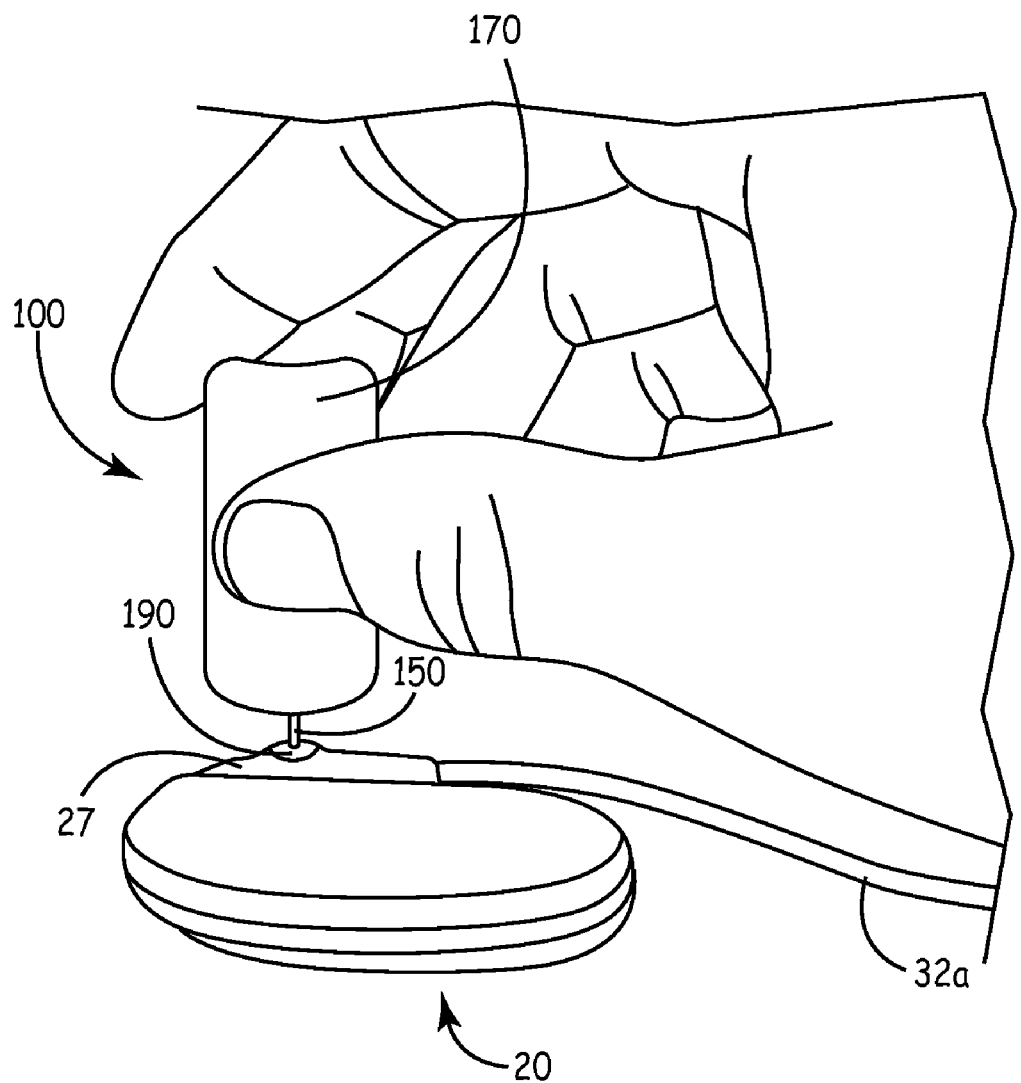
FIG. 2 illustrates an exemplary torque wrench engaged with a setscrew located inside an implantable medical device.

Referring to FIGS. 1-2, an implantable medical device (IMD) 20 can include implantable pacemakers, implantable cardioverter defibrillator (ICD) devices, cardiac resynchronization therapy defibrillator devices, neurostimulators, drug pumps or combinations thereof. Exemplary IMDs are commercially available as including one generally known to those skilled in the art, such as the Medtronic CONCERTOT™, SENSIA™, VIRTUOSO™, RESTORE™, RESTORE ULTRA™, sold by Medtronic, Inc. of Minnesota. IMD 20 can include an implantable case, housing or body assembly 22. Implantable case 22 can be formed of appropriate materials and include appropriate features, such as a hermetically sealed body wall 24a. Body wall 24a comprises substantially conductive material such as titanium.

Contained within or associated with case 22 can be a power device 25 such as one or more batteries and/or capacitors encased in housing or case body wall 24b, a controller assembly 26, and a connector body 27. Controller assembly 26 can include a circuit board having a processor, memory, transmitter, receiver, and/or other appropriate portions. Connector body 27 can extend from or be integrated with case 22. At its distal end, connector body 27 or header can include one or more ports 28a,b that interconnects with one or more connector terminals 30a,b of one or more lead assemblies 32a,b. Exemplary connector bodies 27 can include International Standard-1 (IS-1) connectors, IS-4 connectors or other suitable connectors contained within an insulative body.

Lead assemblies 32a,b can comprise respective lead bodies 34a,b. Lead bodies 34a,b include one or more elongated insulated conductive elements. Each conductive element extends from a proximal end 5 to a distal end 7. In particular, as shown in FIG. 3, a conductive element for the lead assemblies 32a,b has a terminal pin 137 located at the proximal end 5 and, at the distal end 7, an uninsulated portion of a conductive element connects with one of the electrodes such as a ring electrode or a tip electrode 36a,b.

Figure 4A:
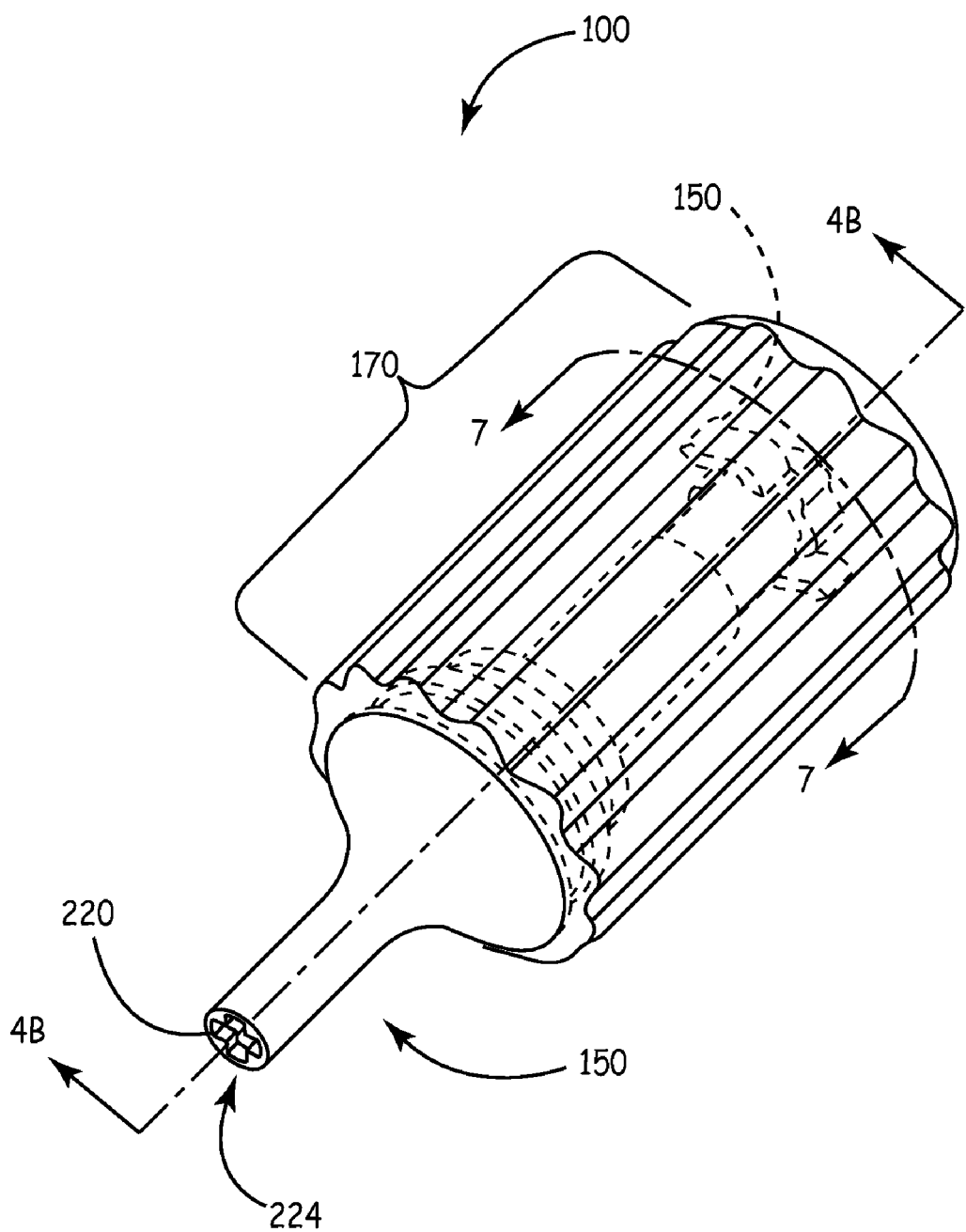
FIG. 4A is a schematic exterior view of an exemplary torque wrench.
Figure 4B:
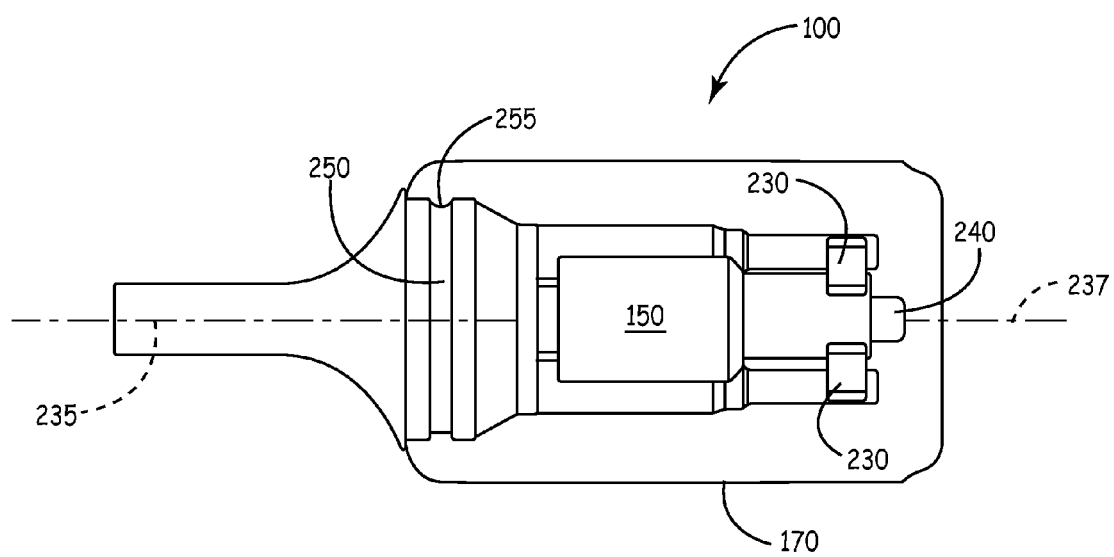
FIG. 4B is a schematic side view of the exemplary torque wrench of FIG. 4A such that the handle is cutaway along lines 4B-4B.
Figure 8:
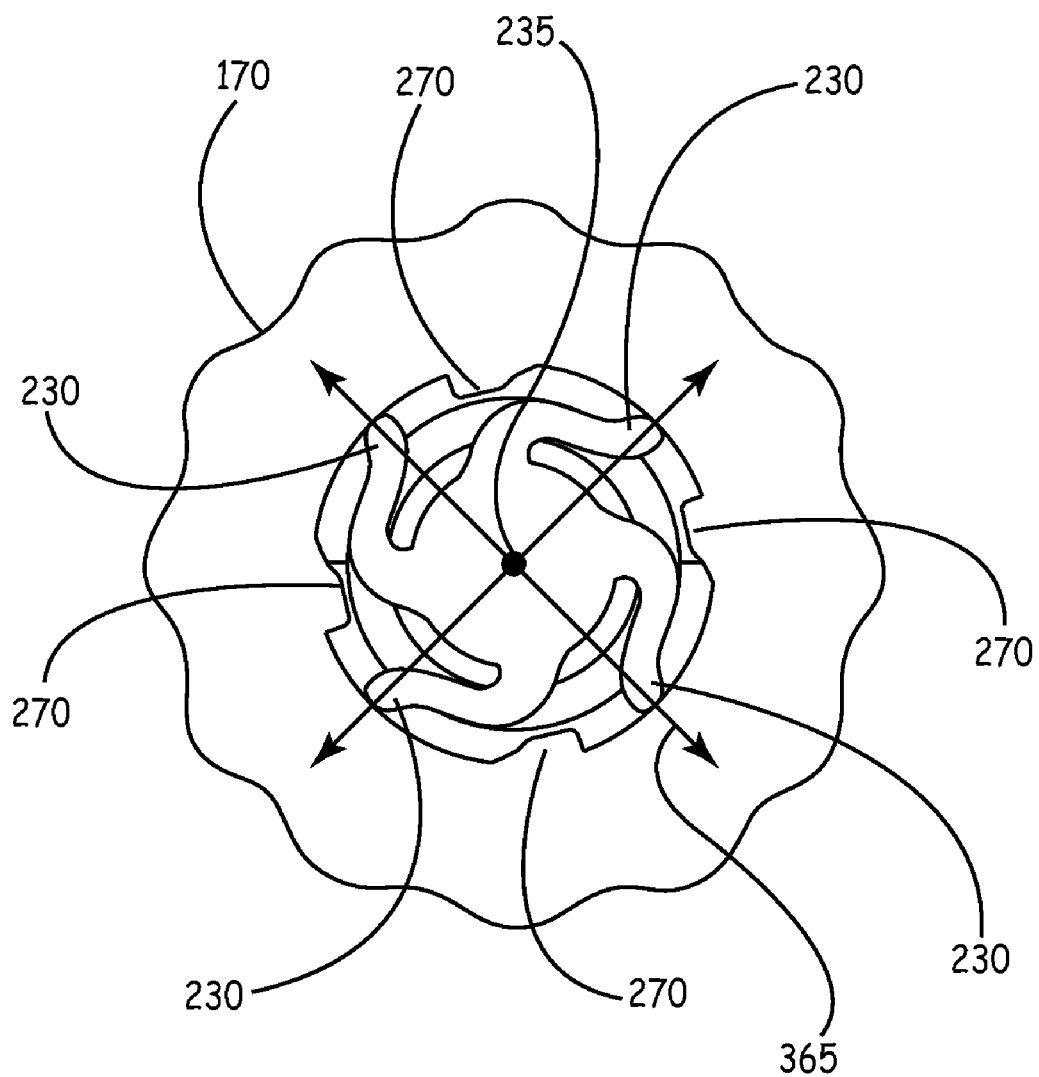
FIG. 8 shows a cutaway view of the torque wrench of FIG. 4A taken along lines 7-7.

To connect a lead body 34a,b to the IMD 20, the terminal pin 137, which extends from lead body 34a,b, is placed through a bore in connector body 27 and inside a setscrew block 160. Connector 200, such as a set screw, is dielectrically insulated from body fluid outside the IMD 10 through a silicone grommet 190. A torque wrench 100 contacts the connector 200 by passing through a slit (not shown) in the grommet 190. An exemplary torque wrench 100 for applying an appropriate amount of torque to connector 200 is depicted in FIGS. 4A-4B. Torque wrench 100 can comprise, or consist of, a handle 170 and a drive shaft member 150 which are used, in combination, to tighten connector 200 onto a terminal pin 137. The proximal end 224 of drive shaft 150 can include an integrally formed drive shaft tool interface 220, which is configured to connect with connector 200. The drive shaft member 150 is positioned within a bore of handle 170 and snaps into place once snap groove 250 of drive shaft member 150 connects with snap protrusion 255 of handle 170. Drive shaft member 150 includes a position member 240 that extends through an aperture (not shown) of handle 170 and positions the drive shaft member 150 to rotate about rotational axis 237. Additionally, flexible fingers 230, which extend from the drive shaft member 150 and substantially protrude in a perpendicular direction relative to the drive shaft axis 235, selectively engage with anti-rotation members 270 (FIG. 5B) that extend from the handle 170. Referring briefly to FIG. 8, the torque wrench handle 170 can then rotate until its anti-rotation members 270 connect with the flexible fingers 230 on the drive shaft member 150. Further rotation of handle 170 allows torque to be applied to connector 200 until connector 200 is sufficiently tightened against terminal pin 137, as depicted in FIG. 2. While connector 200 is shown as a setscrew, connector 200 can also be a nut, bolt or other suitable fastener.

FIGS. 5A-5E depict a handle 170. In one or more embodiments, handle 170 can be a cylindrically-shaped body with an inner wall 174 that forms a bore 176 extending from a distal end 175 (second end) to a proximal end 177 (first end) and an exterior surface 184 configured to be held between at least two fingers of a user's hand. The proximal end 177 is closest to the drive shaft tool interface 220 whereas the distal end 175 is farthest from the drive shaft tool interface 220.

A plurality of anti-rotation members 270 or protrusions are formed on the inner wall 174 of handle 170 near or at the distal end 175. For example, anti-rotation members 270 can be located from about 0.05 inches to about 1.5 inches from an edge 244 at the distal end 175. In other embodiments, anti-rotation members 270 can be located from about 0.01 inches to about 2.5 inches from an edge 244 at the distal end 175. In other embodiments, anti-rotation members 270 can be located from about 0 inches to about 5 inches from an edge 244 at the distal end 175.

Figure 5A:
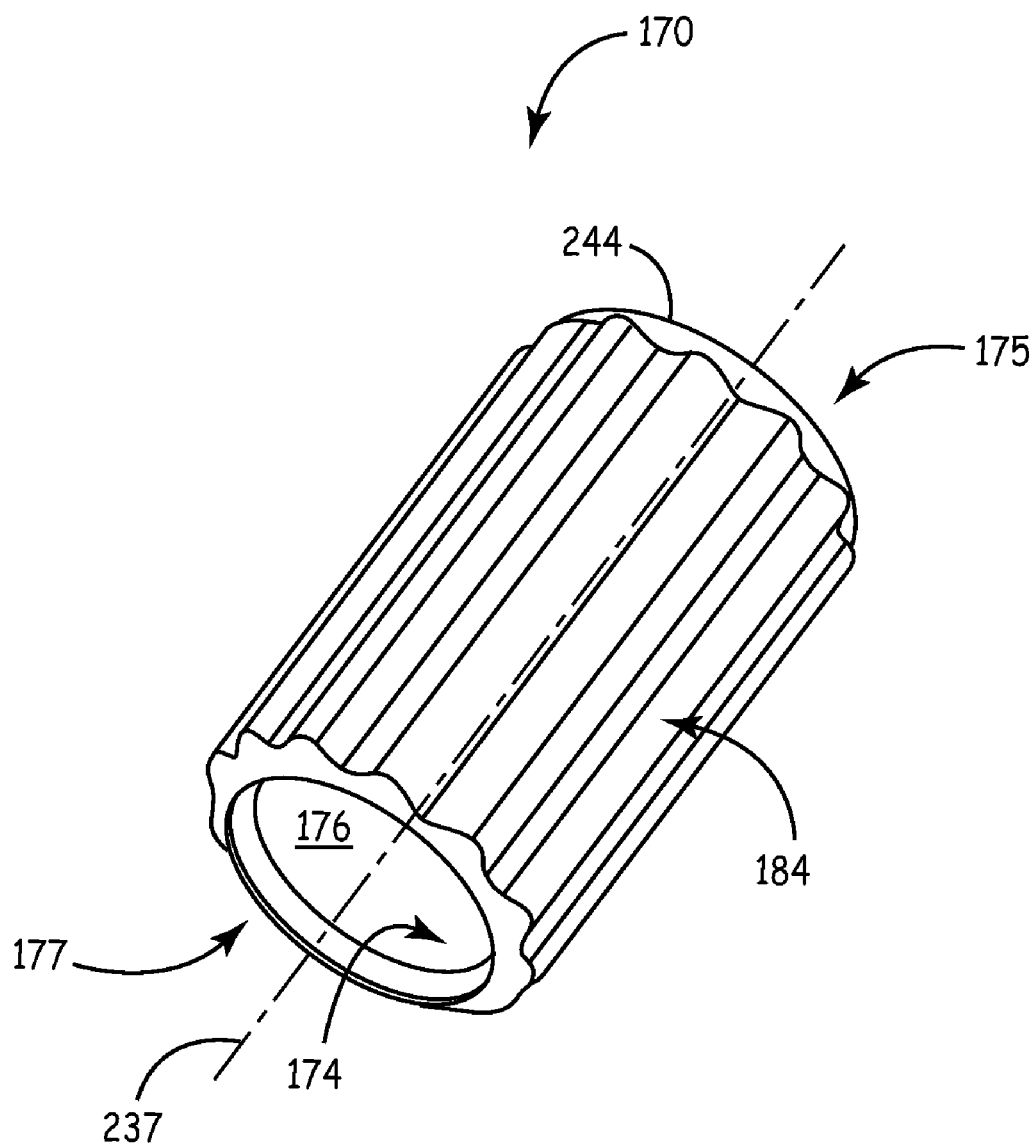
FIG. 5A is a schematic exterior view of the exemplary handle depicted in FIGS. 4A-4B.
Figure 5B:
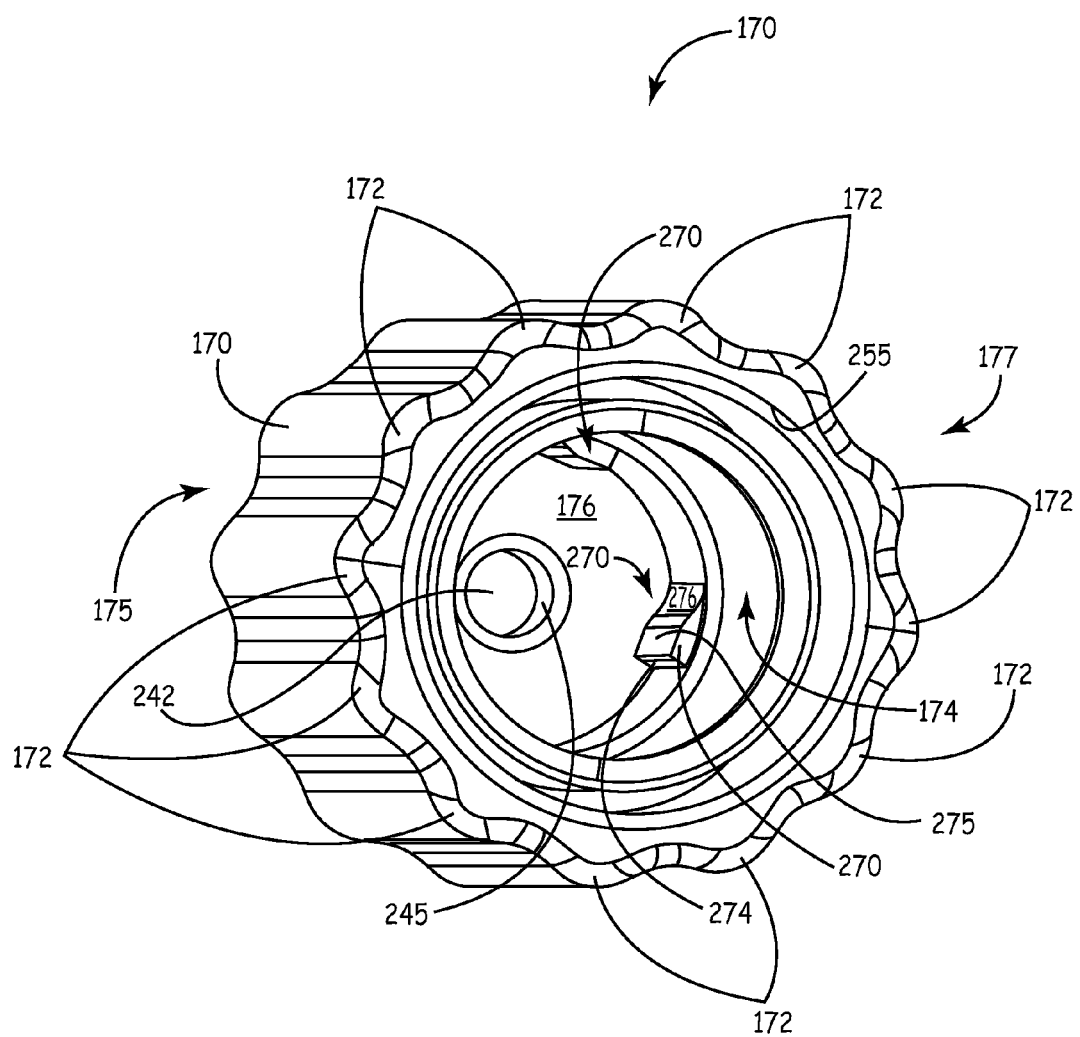
FIG. 5B is a schematic interior view of an exemplary handle.

As depicted in FIG. 5B, anti-rotation members 270 can include a surface 274, flat surfaces 275 and a curved end 276. Surface 274, which can be flat, or, substantially flat, is directly contacted by a distal portion 236 of fingers 230 of drive shaft member 150 while curved end 276 provides sufficient rigidity to secure anti-rotation members 270 in position. The distal portion 236 of fingers 230 can also contact flat surfaces 275 and/or curved end 276.

Figure 5C:
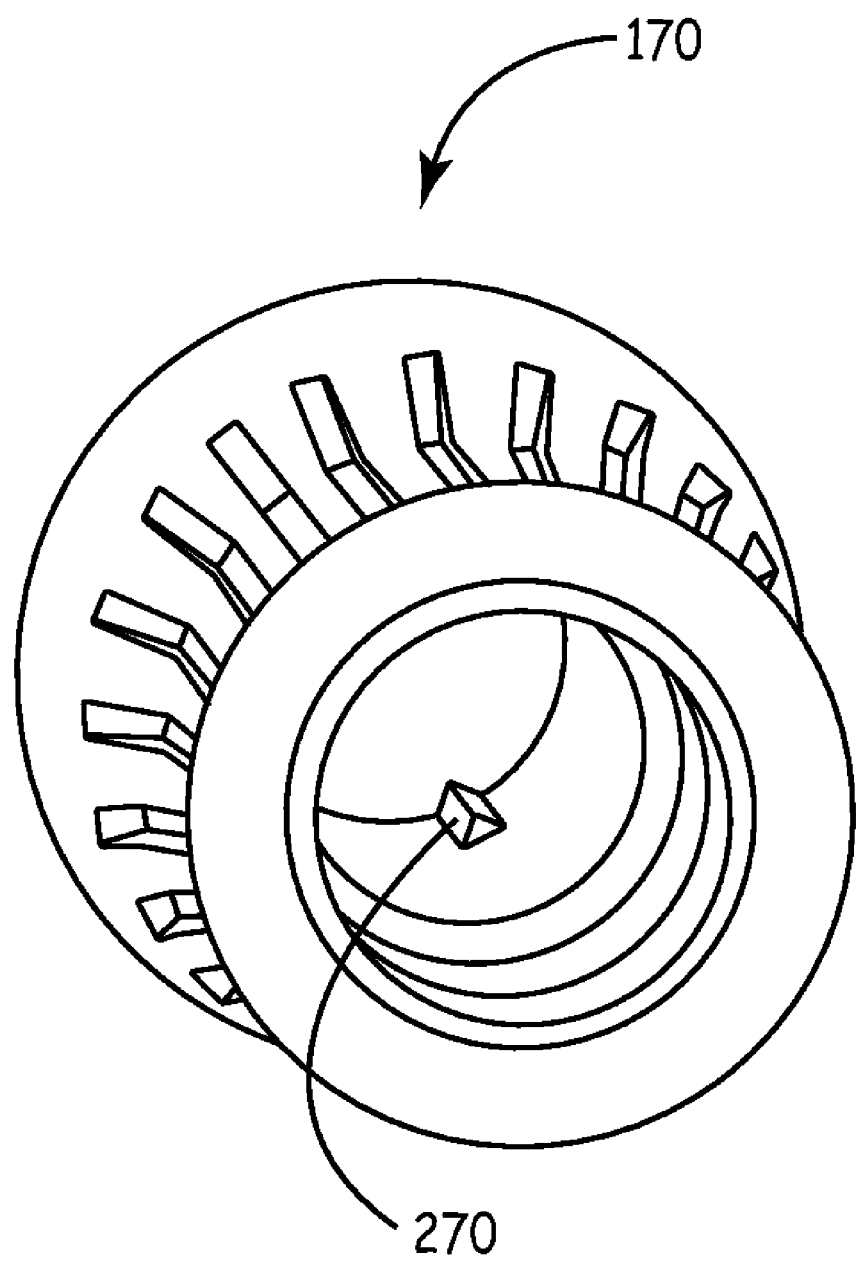
FIG. 5C is a schematic view of a triangular-shaped anti-rotation member located on an inner diameter of another exemplary handle.
Figure 5D:
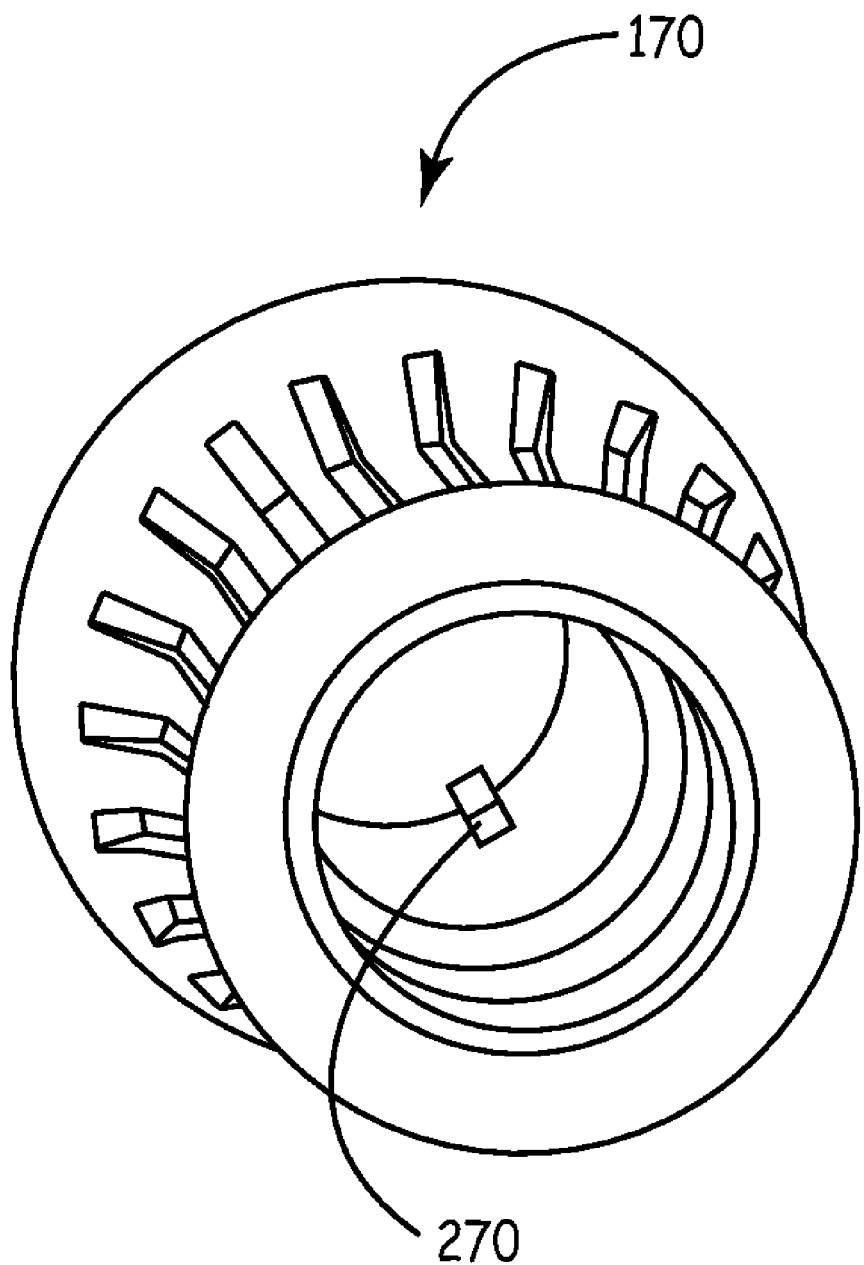
FIG. 5D is a schematic view a rectangular-shaped anti-rotation member located on an inner diameter of yet another exemplary handle.
Figure 5E:
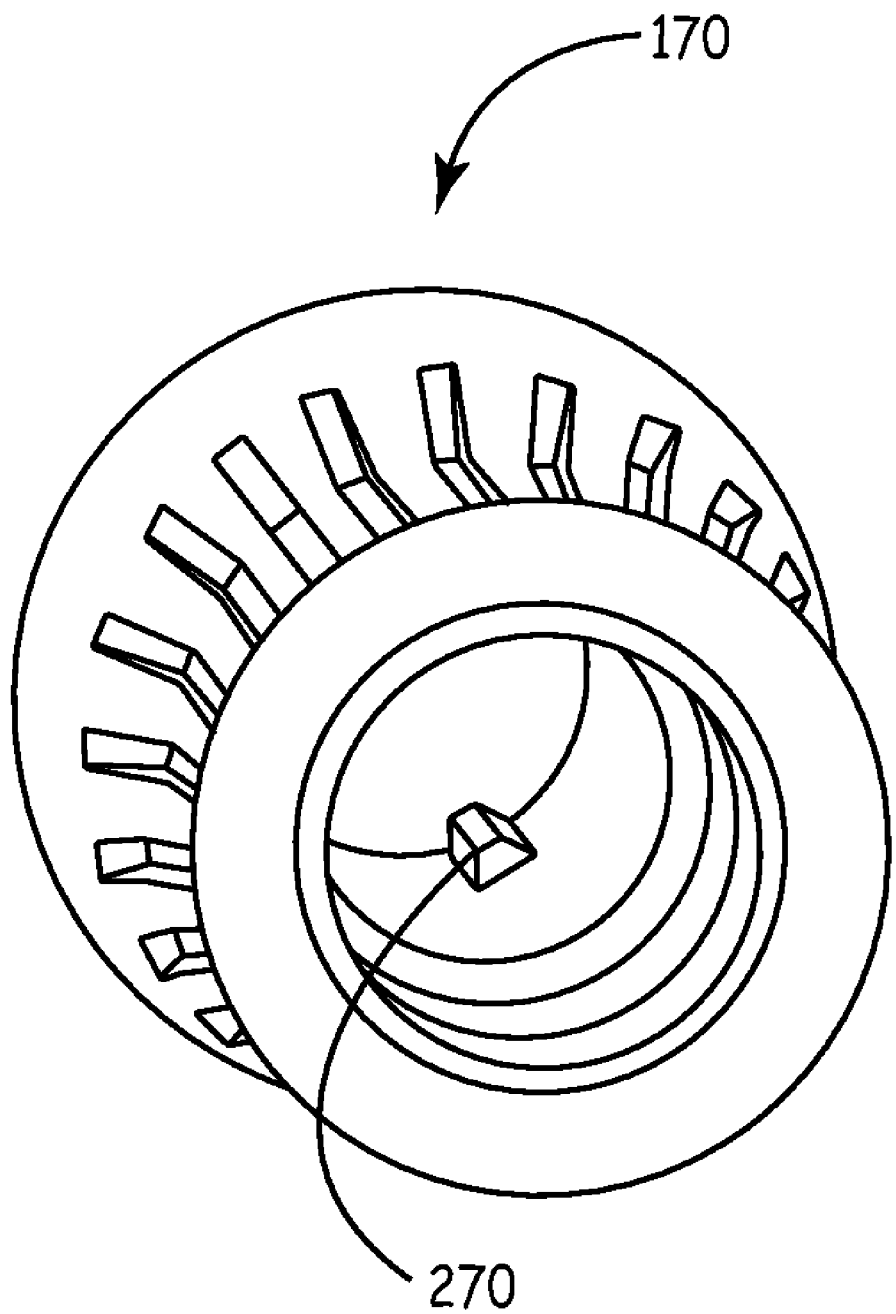
FIG. 5E is a schematic view of a half-circle shaped anti-rotation member located on an inner diameter of yet another exemplary handle.

Anti-rotation members 270, extending into bore 176, can be formed by a variety of shapes. For example, anti-rotation members 270 can possess a shape that is substantially elliptical, substantially cylindrical, substantially rectangular, substantially triangular or other suitable shapes. FIG. 5C depicts an anti-rotation member 270 with a substantially triangular cross-section. Substantially triangular can involve an anti-rotation member within 20 percent of a precise triangular shape. FIG. 5D depicts an anti-rotation member 270 with a substantially rectangular cross-section. FIG. 5E depicts an anti-rotation member 270 with a substantially half-circle cross-section.

Figure 5F:
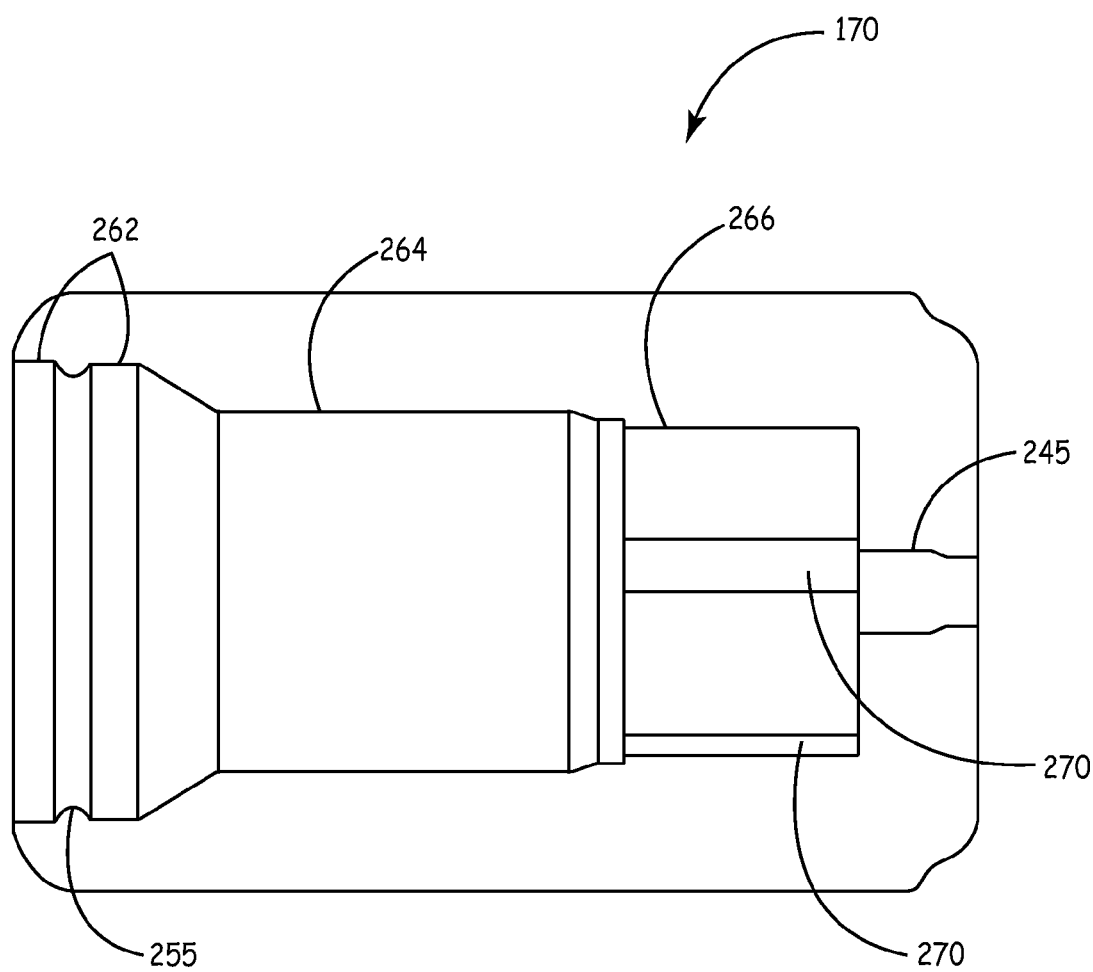
FIG. 5F is a schematic side view of the exemplary handle of FIG. 4A such that the handle is cutaway along lines 4B-4B.

Handle 170 can further include a plurality of inner diameters in order to receive and secure drive shaft member 150 within bore 202. For example, as shown in FIG. 5F, the plurality of inner diameters can include a first inner diameter 262 (ID1), a second inner diameter 264 (ID2), a third inner diameter 266 (ID3), and a fourth inner diameter 245 (ID4). Exemplary diameters are presented below in table 1; however, other sizes can also be used.

TABLE 1

Exemplary dimensions for a handle (dimensions in inches)

| | ID1 | ID2 | ID3 | ID4 |
|---|---|---|---|---|
| Embodiment 1 | 0.25 to 0.35 | 0.20 to 0.25 | 0.20 to 0.25 | 0.10 to 0.15 |
| Embodiment 2 | 0.15 to 0.50 | 0.10 to 0.50 | 0.10 to 0.50 | 0.05 to 0.50 |
| Embodiment 3 | 0.10 to 1 | 0.10 to 1 | 0.10 to 1 | 0.05 to 1 |
| Embodiment 4 | 0.01 to 4 | 0.01 to 4 | 0.01 to 4 | 0.01 to 4 |

Figure 9:
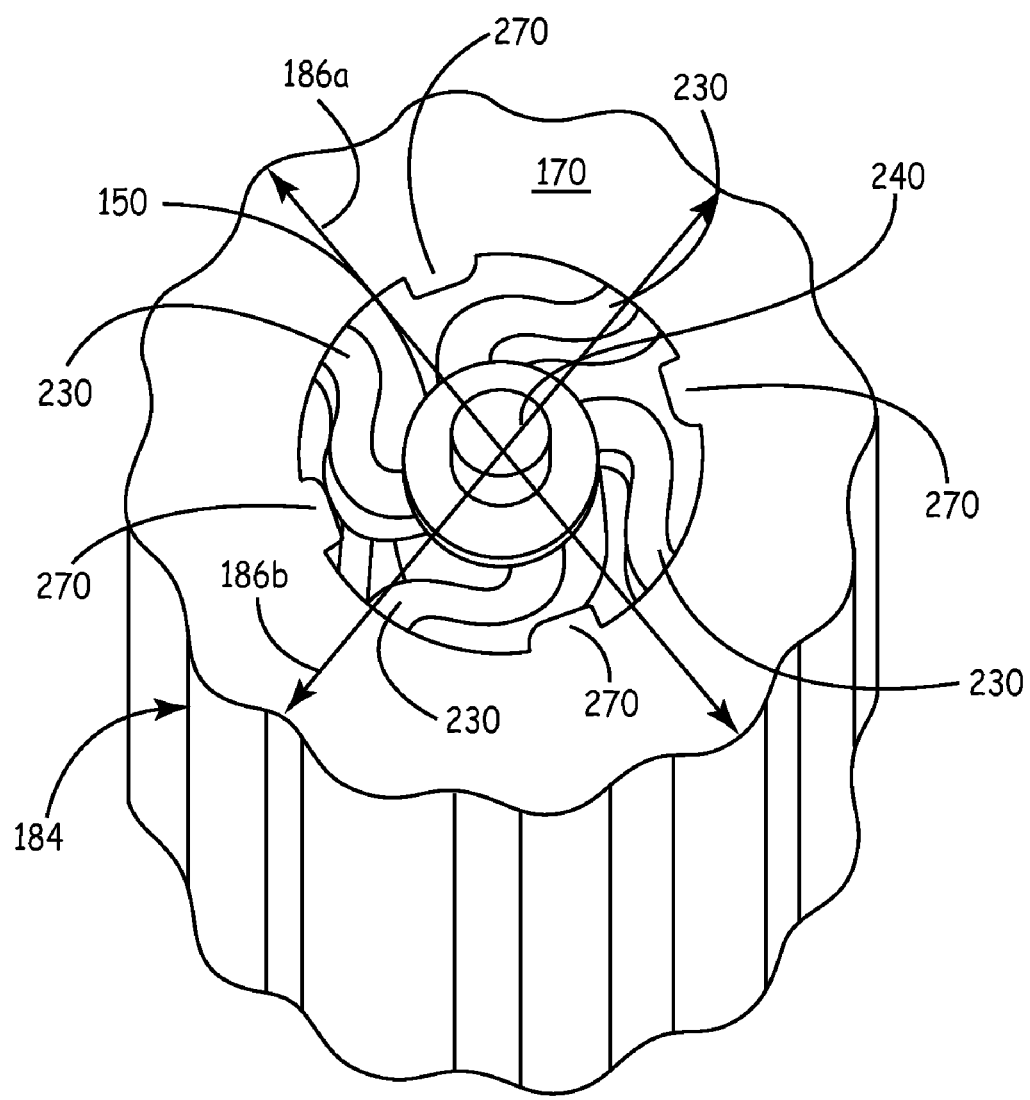
FIG. 9 shows a schematic view of the torque wrench of FIG. 4A such that the handle is cutaway along lines 7-7.

Referring to FIGS. 4A-5E, the exterior surface 184 of the handle 170 can include gripping elements. For example, FIG. 5B depicts protrusions 172 such as convex protrusions in handle 170 can aid in gripping the handle 170. Recessed regions or concave regions in handle 170 can also be used to allow a user to better grip handle 170. The convex protrusions or recessed regions can be elongated, short and/or small dots. Referring briefly to FIG. 9, the outer diameter 186a,b of the handle 170 can vary along the handle's 170 rotational axis 237 to provide enhanced gripping features. In some embodiments, outer diameter 186a,b can range from about 0.3 inches to about 1.2 inches. In other embodiments, outer diameter 186a,b can range from about 0.1 inches to about 2.5 inches. In yet other embodiments, outer diameter 186a,b can range from about 0.05 inches to about 3.5 inches.

Figure 6A:
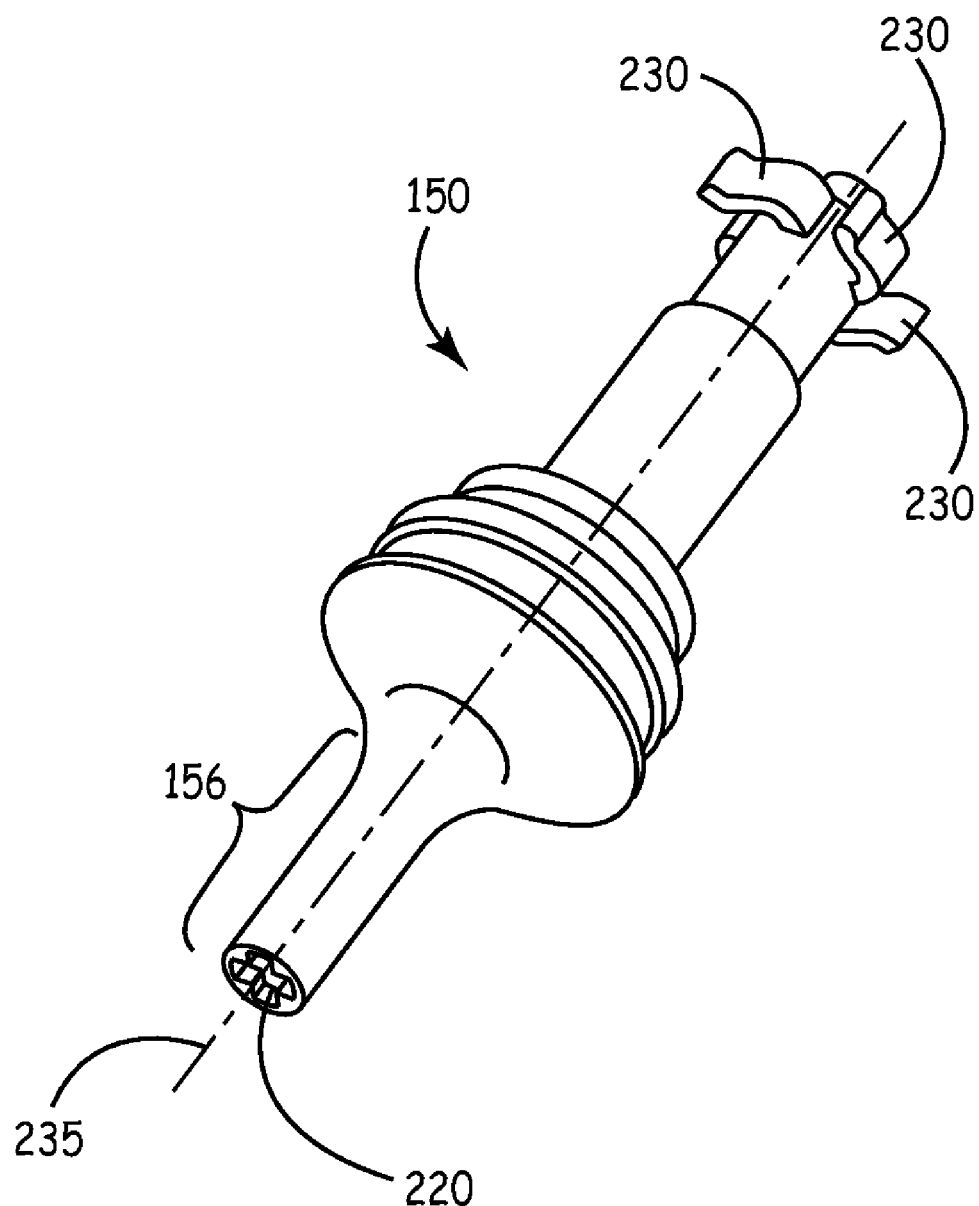
FIG. 6A is a schematic view of an exemplary drive shaft member.
Figure 6B:
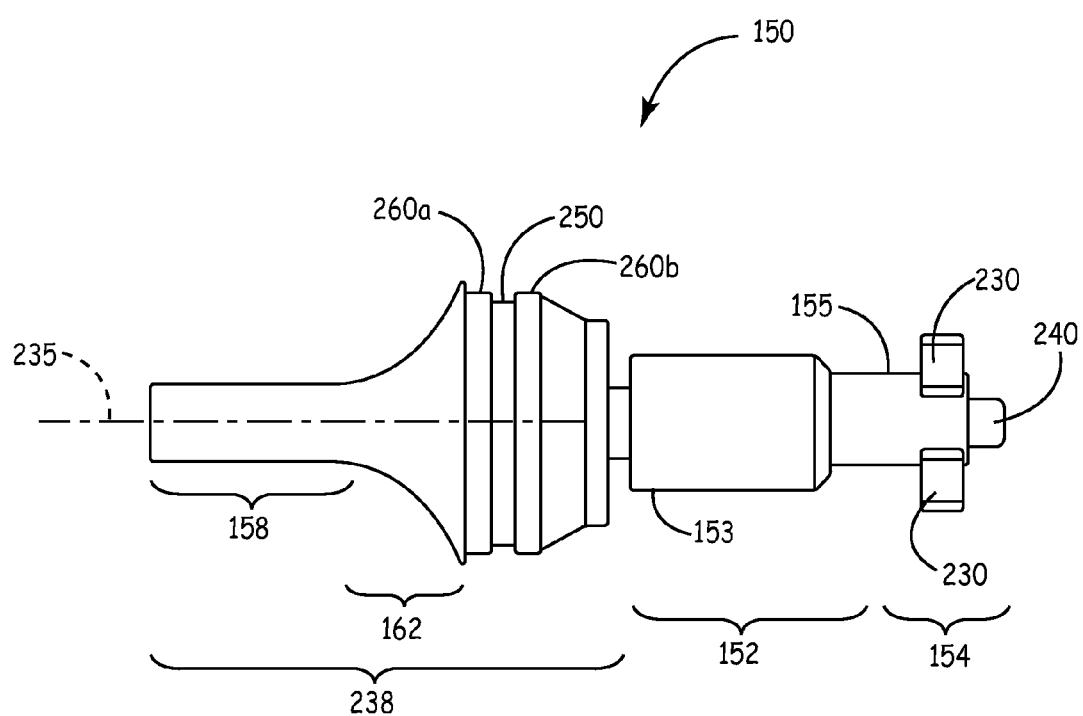
FIG. 6B shows a schematic side view of an exemplary drive shaft member.
Figure 6C:
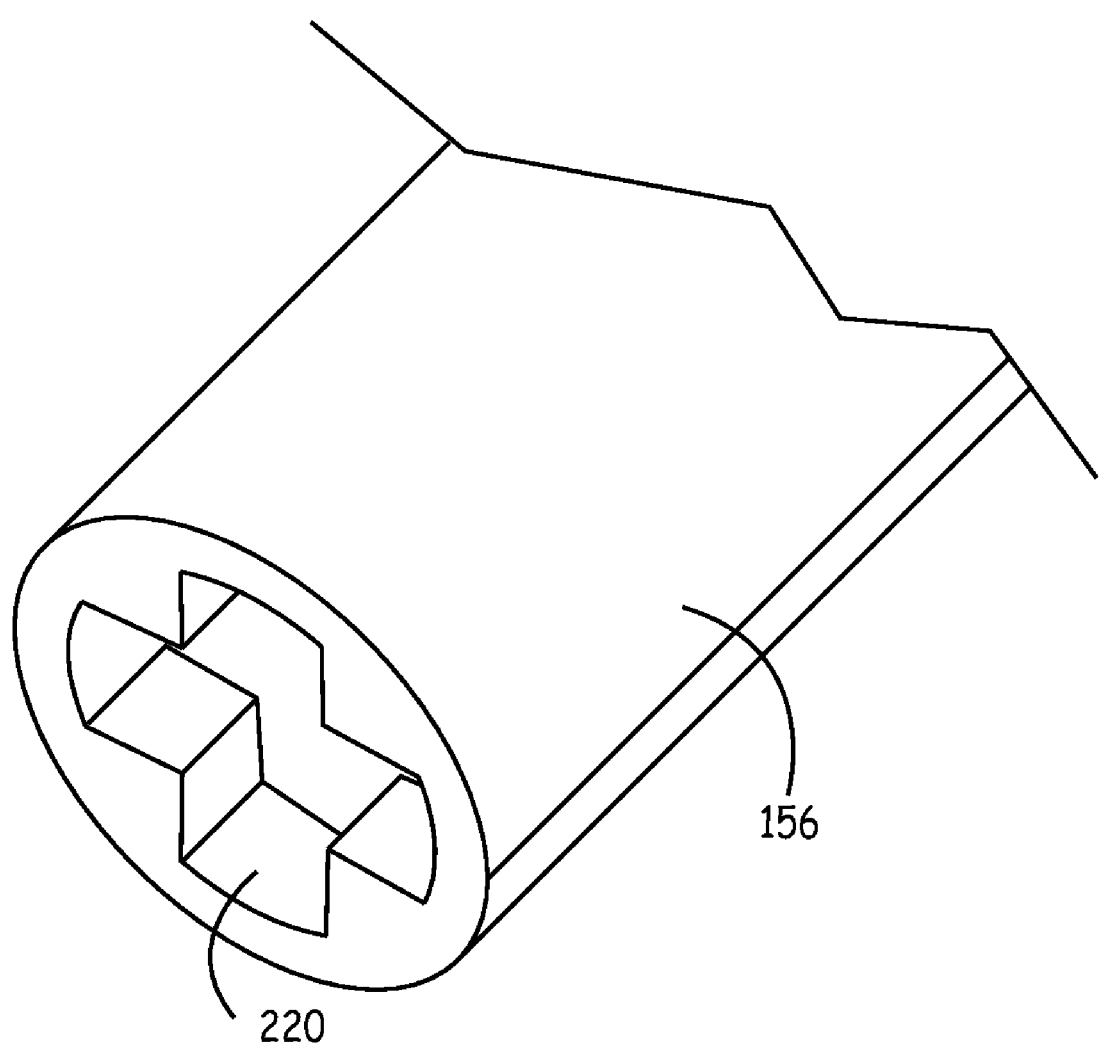
FIG. 6C is a schematic view of an exemplary drive shaft tool interface.
Figure 7:
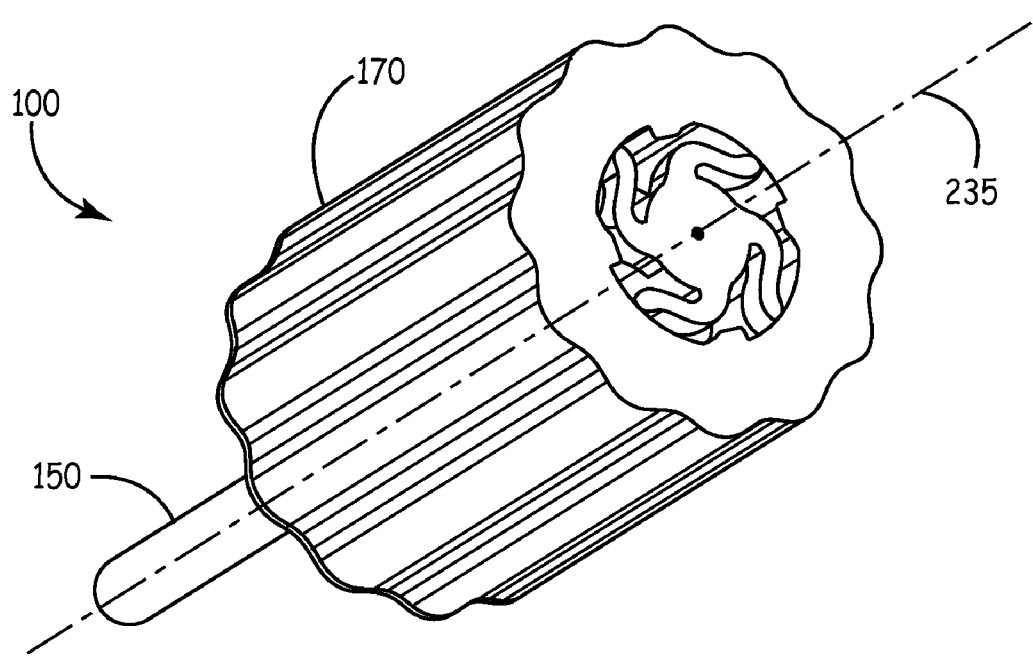
FIG. 7 shows a schematic cutaway view of the torque wrench of FIG. 4A taken along lines 7-7.

Referring to FIGS. 6A-6C, drive shaft member 150 comprises a first end 238 (the drive shaft end), a middle portion 152, and a second end 154. In one or more embodiments, first end 238, middle portion 152, and second end 154 are integrally formed together. First end 238 includes a drive shaft tool interface 220, a drive shaft 156, a snap groove 250, and drive shaft surface 260a,b. Drive shaft 156 is preferably integrally formed to drive shaft member 150. In one embodiment, a rigid tool interface is formed by a drive shaft 156 material that can be more rigid than the material used for the rest of the drive shaft member 150. For example, the rigid tool interface can comprise a metal or alloy while the rest of the drive shaft member 150 could be a polymer such as plastic. Exemplary polymers can include acrylonitrile butadiene styrene (ABS) polyetherimide (PEI) manufactured by SABIC Innovative Plastics located in Houston, Tex.) and polyaryletheretherketone PEEK commercially available from Solvay located in Houston, Tex.

In one embodiment, a metal drive shaft 156 is insert molded into a plastic body in which the drive shaft 156 and the plastic body together form the drive shaft member 150. In this embodiment and in other embodiments, the flexible fingers 230 can be integrally formed as part of the drive shaft member 150 during the molding process.

Drive shaft tool interface 220, depicted in FIG. 6C, is integrally or separately formed to drive shaft 156. Drive shaft tool interface 220 can include a distal side (not shown) located adjacent to drive shaft 156, and a proximal side 224 as shown in FIG. 4A. The proximal side 224 directly touches or contacts the connector 200. Proximal side 224 of torque wrench tool interface 220 is configured to securely attach to an opposing exterior surface of connector 200. Many torque wrench tool interfaces 220 can be applied to one or more of the embodiments described herein. Tool interface 220 can be configured to connect with a variety of screw drives disposed on connector 200. Exemplary screw drive types can be slotted, Philips, hex, torx, spanner head, triple square or other suitable types.

Referring to FIG. 6B, drive shaft 156 comprises a longitudinal element 158 integrally formed with a base portion 162 that can be flared. Longitudinal element 158 is typically solid and can possess a diameter that ranges from about 0.01 inches to about 0.5 inches. In typical embodiments, the longitudinal element 158 possesses a diameter that ranges from about 0.025 inches to about 0.2 inches. The length of the longitudinal element 158 can range from about 0.01 inches to about 5 inches. In typical embodiments, the length of the longitudinal element 158 can range from about 0.1 inches to about 2 inches. Base portion 162 is proximal to drive shaft bearing surfaces 260*a,b* and snap groove 250. More particularly, base portion 162 is closer to the torque wrench tool interface 220 than drive shaft bearing surfaces 260*a,b* and snap groove 250. Snap groove 250 can include an outer diameter that ranges from about 0.01 inches to about 4 inches. In typical embodiments, snap groove 250 can include an outer diameter that ranges from about 0.2 inches to about 1.5 inches.

Middle portion 152 comprises a body portion 153 with a variety of outer diameters in order to support and securely connect to handle 170. Outer diameters can include outer diameter one (OD1), outer diameter two (OD2), and outer diameter three (OD3) which can couple with ID1, ID2, and ID3, respectively of handle 170. The inner diameter 262, 264, 266, 245 dimensions, that define the interior geometry of the handle 170, are at least slightly larger than the corresponding outer diameter OD1-OD4 dimensions of the drive shaft member 150 such that the drive shaft member 150 is able to spin freely relative to the handle 170 unless the flexible fingers 230 collide or contact the anti-rotation members 270. Spin freely occurs when a torque that is less than half of the breakaway torque is able to cause the drive shaft member 150 to rotate relative to the handle 170. Exemplary outer diameter dimensions for drive shaft 156 are presented below in Table 2.

TABLE 2

Exemplary dimensions for a drive shaft (dimensions in inches)

|  | OD1 | OD2 | OD3 | OD4 |
|---|---|---|---|---|
| Embodiment 1 | 0.24 to 0.34 | 0.19 to 0.24 | 0.19 to 0.24 | 0.09 to 0.14 |
| Embodiment 2 | 0.14 to 0.49 | 0.09 to 0.49 | 0.09 to 0.49 | 0.04 to 0.49 |
| Embodiment 3 | 0.09 to 0.99 | 0.09 to 0.99 | 0.09 to 0.99 | 0.04 to 0.99 |
| Embodiment 4 | 0.009 to 3.99 | 0.009 to 3.99 | 0.009 to 3.99 | 0.009 to 3.99 |

The second end 154 includes a position member 240 (referred to as a position cylinder) and a plurality of flexible fingers 230. Position member 240, shaped as a cylinder, is configured to extend through an aperture 242 so that position member 240 can rotate. The inner diameter of the position aperture 245 is slightly larger than the outer diameter of the position cylinder 240.

As shown, plurality of fingers 230 comprise at least four fingers 230, however, any number of fingers 230 can be used. For example, one or more fingers 230 can be used on the second end 154 of the drive shaft member 150. In one or more embodiments, the plurality of fingers 230 are symmetrically spaced apart from each other. In another embodiment, plurality of fingers 230 are asymmetrically spaced apart from each other.

Referring to FIGS. 6A-6B, and 7-13, flexible fingers 230 are sized such that flexible fingers 230 typically are unable to touch any part of the handle 170 except the anti-rotation members 270. The drive shaft member 150 has a plurality of flexible fingers 230 extending from an exterior surface. While flexible fingers 230 can follow a tortuous path; in one or more embodiments, fingers 230 protrude in a perpendicular or substantially perpendicular direction relative to the drive shaft axis 235 such that the generally flat proximal portion of fingers 230 typically point in a direction that is away from the drive shaft axis 235. Substantially perpendicular includes perpendicular plus or minus 50 degrees relative to drive shaft axis 235. In other embodiments, the flexible fingers extend from an exterior surface that is not substantially perpendicular.

Figure 11:
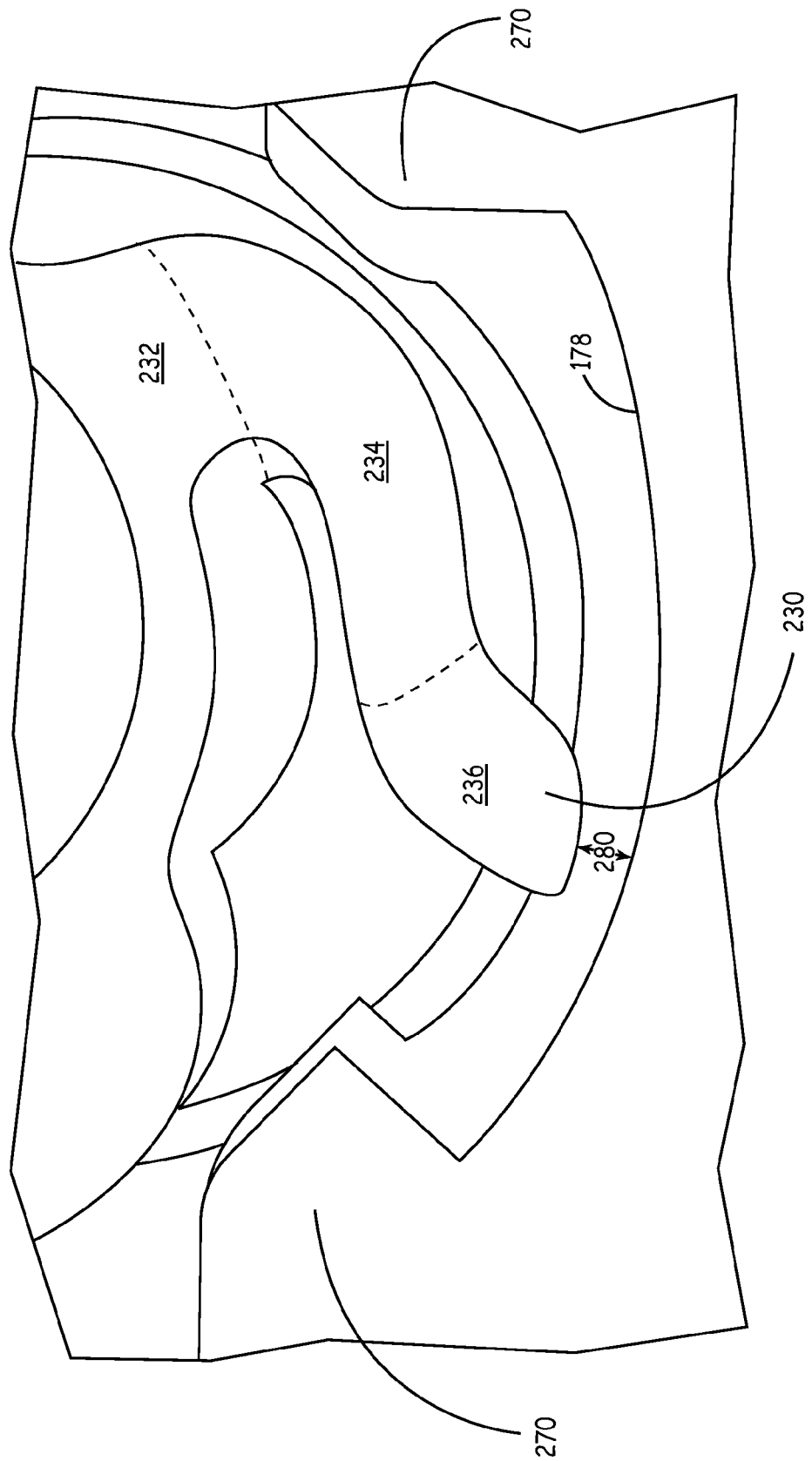
FIG. 11 depicts a top schematic view of a flexible finger relative to an inner wall of the handle for the torque wrench.

Referring to FIGS. 6B and 11, each relaxed flexible finger 230 comprises a first portion 232, a second portion 234, and a third portion 236, each of which can be integrally formed as a single finger. In one or more embodiments, the flexible fingers 230 attach to the first portion base 155 of the drive shaft member 150. First portion 232 extends radially away from the drive shaft axis 235 of drive shaft member 150. The drive shaft axis 235 runs through the middle of the drive shaft member 150 from the first end 238 to the second end 154.

Second portion 234 is integrally formed to first and third portions 232, 236, respectively. In one or more embodiments, second portion 234 can be curved. In some embodiments, the angle between the first portion 232 and the second portion 234 ranges from 0 degrees to 120 degrees. In some embodiments, third portion 236 (also referred to as a distal portion, gripping portion or a coupling portion) is substantially perpendicular to first and/or third portions 232, 236, respectively. Second portion 234 typically can move up to 90 degrees from a relaxed position to a stressed position. In some embodiments, second portion 234 can move up to 150 degrees from a relaxed position to a stressed position. In typical embodiments, each finger 230*a-d* possesses the flexibility to elastically deform until the finger 230 touches the surface of the drive shaft member 150 from which the finger 230 extends and then spring back to about the finger's 230 relaxed position without breaking. The fingers 230 do not include a helical spring like conventional torque wrenches.

Polymeric material can be used to form the flexible fingers 230 as well as the remaining portions of drive shaft member 150. Typically, the polymeric material selected for forming flexible fingers 230 provides sufficient flexibility such that fingers 230 do not relax or creep over time due to compressive forces imparted from the handle 170 on the flexible fingers 230 when the torque wrench 100 is not in use. Exemplary material that can be used to form fingers 230 can include polyetherimide (PEI), although other polymeric material can be used such as polyaryletheretherketone (PEEK), acrylonitrile butadiene styrene (ABS). Other suitable polymers can also be used. In one or more embodiments, the flexible finger 230 can bend toward the drive shaft axis 235 in order to rotate or move past the anti-rotation member 270.

A fully assembled exemplary torque wrench 100 is depicted in FIGS. 4A-B. In one or more embodiments, the drive shaft member 150 and the handle 170 are assembled by simply pushing the drive shaft member 150 into the proximal end 177 of opening or bore 176 located in the handle 170, which is closest to the snap protrusion 255. Drive shaft member 150 can be rotated or moved while being pushed into handle 170 so that the plurality of fingers 230 are positioned interdigitate with the anti-rotation members 270. Once the snap protrusion 255 of handle 170 resides in the snap groove 250 and the position cylinder 240 resides in the position aperture 242, the torque wrench 100 is fully assembled.

The small clearance or gap (not shown) between the drive shaft bearing surfaces 260 and the handle bearing surfaces 265 and the small gap (not shown) or clearance between the position cylinder 240 and the position aperture 242 ensures the drive shaft axis 235 is generally aligned with the handle axis 237 even when the handle 170 rotates relative to the drive shaft member 150. The assembler or user can then verify that handle 170 is able to rotate relative to the drive shaft member 150. The handle axis 237 runs through the middle of the handle 170 from the distal end 175 to a proximal end 177.

To rotate handle 170, torque is applied between the drive shaft member 150 and the handle 170, which causes the flexible fingers 230 to contact the anti-rotation members 270. If breakaway torque is applied, the flexible fingers 230 can elastically deform and bend sufficiently to move past the anti-rotation members 270. Breakaway torque is a maximum level of torque that torque wrench 100 can apply between the handle 170 and the drive shaft member 150. For example, a torque wrench 100 can have a breakaway torque of 14 ounce-inches. In this case, a user could apply any torque from 0 ounce-inches up to 14 ounce-inches. If the user applied a torque less than 14 ounce-inches and the handle 170 was engaged with the drive shaft member 150, the handle 170 would not rotate more than 360 degrees relative to the drive shaft member 150. An applied torque that is equal to or greater than the breakaway torque can cause flexible fingers 230 to sufficiently bend and move past the anti-rotation members 270 such that the handle 170 can rotate more than 360 degrees relative to the drive shaft member 150. If a user tried to apply a torque greater than 14 ounce-inches, the handle 170 would begin to rotate relative to the drive shaft member 150, thus limiting the maximum level of torque the user could apply to approximately 14 ounce-inches. Once a user has applied the breakaway torque between the torque wrench 100 and the connector 200 to tighten the connector 200 onto the terminal pin 137, the lead 32a is securely joined with the header 140, as shown in FIG. 2.

Figure 10A:
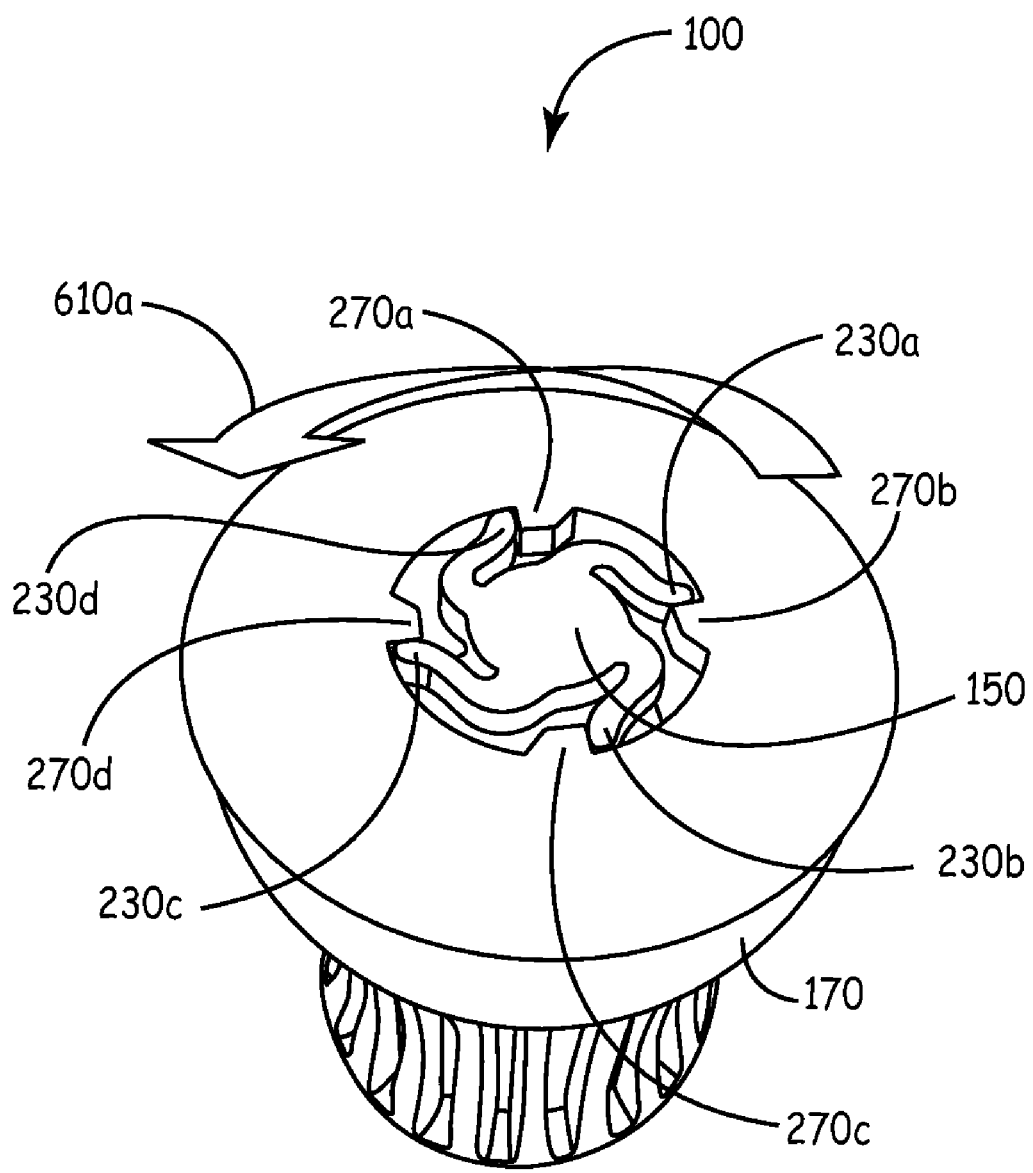
FIG. 10A depicts a top schematic view of an exemplary torque wrench in which the handle is rotated counterclockwise until flexible fingers for the drive shaft member engage anti-rotation members in the handle.
Figure 10B:
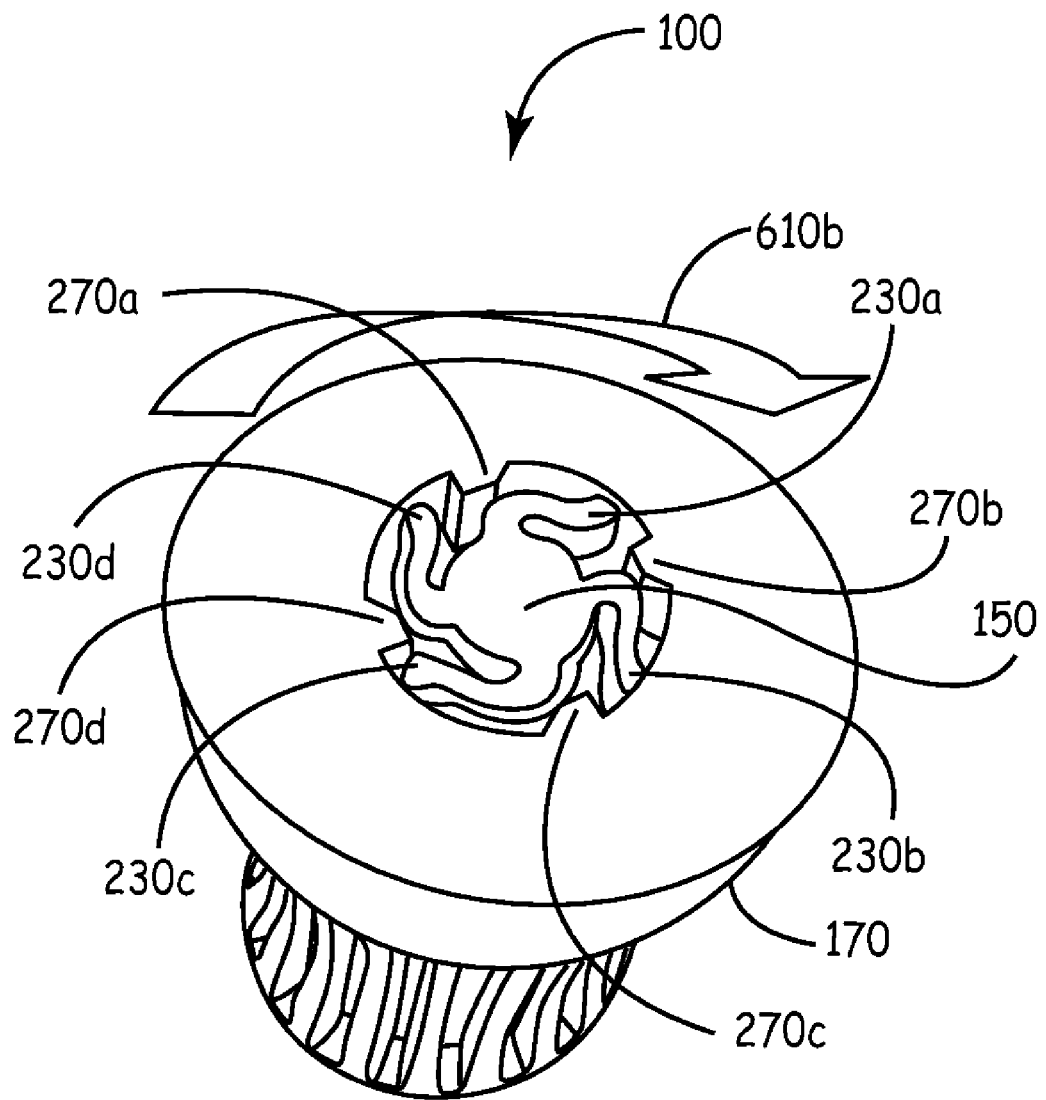
FIG. 10B depicts a top schematic view of the exemplary torque wrench depicted in FIG. 10A in which the handle is rotated clockwise to disengage flexible fingers from the anti-rotation members in the handle.

FIGS. 10A-D depict rotation of the drive shaft member 150 within handle 170. These figures also show the flexibility of each finger 230a-d, each of which lack a helical spring. The drive shaft member 150 remains substantially stationary while handle 170 rotates, which causes plurality of fingers 230a-d to move. For example, as shown in FIG. 10A, plurality of fingers 230a-d, placed interdigitate with the anti-rotation members 270a-d within the bore of the handle 170, are locked against anti-rotation members 270a-d. As handle 170 rotates, the position of each finger 230a-d moves relative to anti-rotation member 270a-d. A gap 280 exists between inner wall 178 of handle 170 and third portion 236 of each finger 230 as depicted in FIG. 11. While handle 170 continues to be rotated counterclockwise, plurality of fingers 230a-d engage anti-rotation members 270. In this position, anti-rotation members 270 prevent plurality of fingers 230a-d from moving further in the counterclockwise direction. Referring to FIG. 10B, handle 170 is then rotated clockwise, which unlocks plurality of fingers 230 from anti-rotation members 270.

Figure 10C:
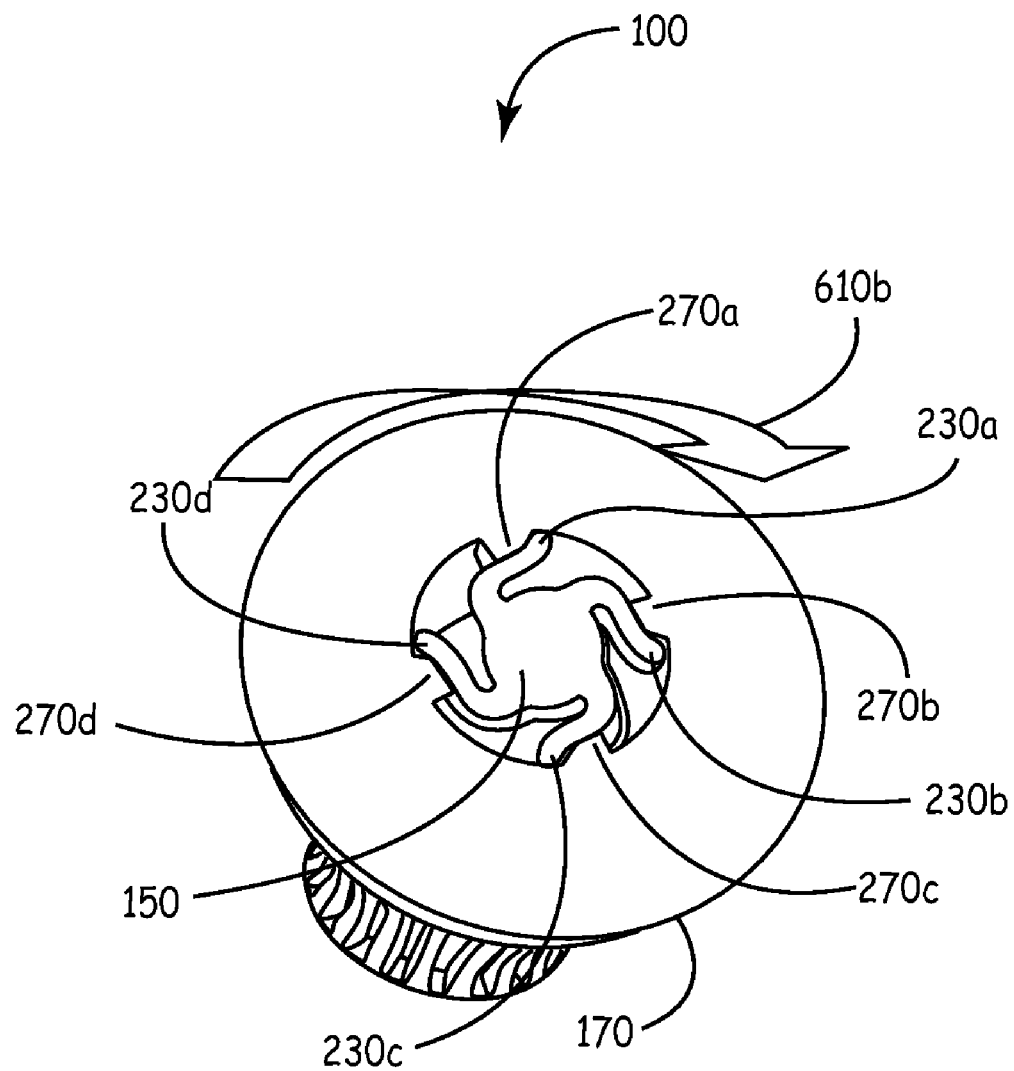
FIG. 10C depicts a top schematic view of the exemplary torque wrench depicted in FIG. 10B in which the handle is again rotated clockwise so that flexible fingers engage the anti-rotation members in the handle.
Figure 10D:
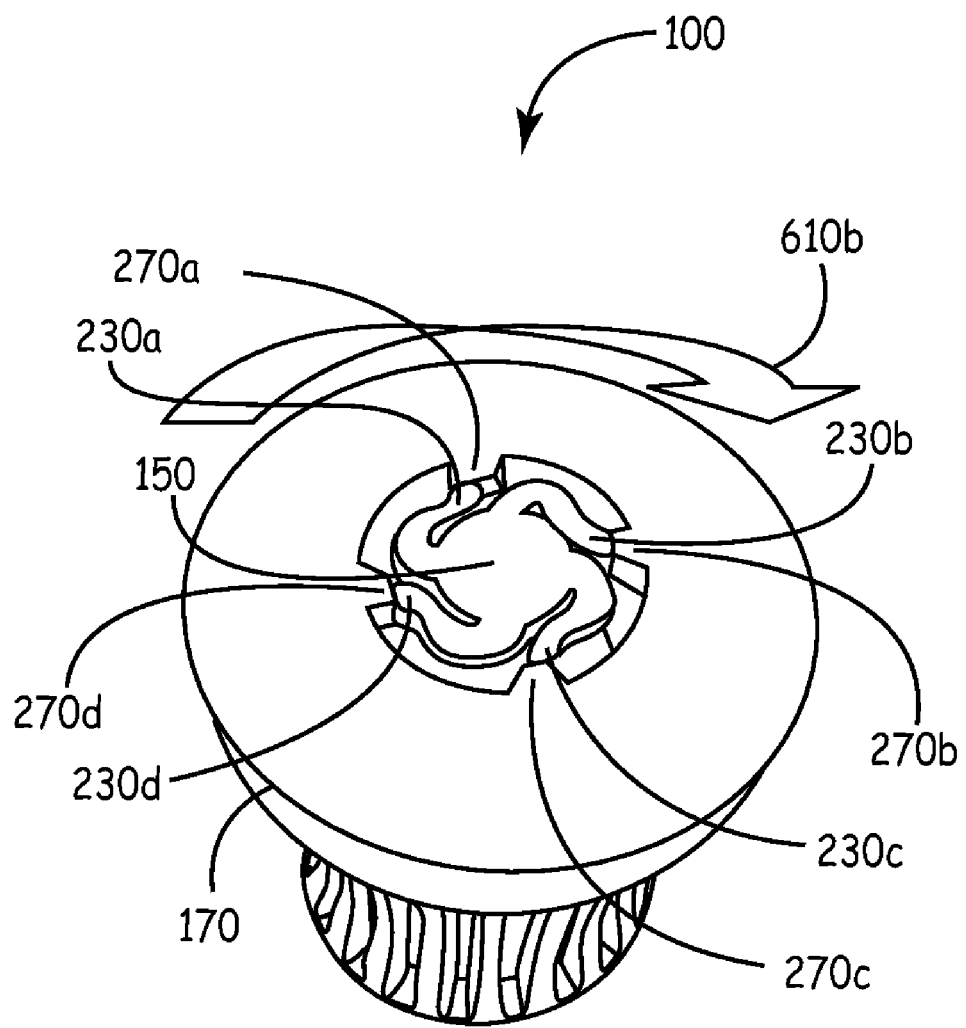
FIG. 10D depicts a top schematic view of the exemplary torque wrench depicted in FIG. 10C in which the handle is again rotated clockwise such that a breakaway torque is applied and flexible fingers begin to rotate past the anti-rotation members in the handle.

FIG. 10C depicts handle 170 rotating slightly clockwise while the drive shaft member 150 remains stationary, which engages plurality of fingers 230a-d with anti-rotation members 270. Further clockwise rotation of handle 170, as shown in FIG. 10D, causes the plurality of fingers 230a-d to begin to rotate past anti-rotation members 270 as a breakaway torque is applied to the handle 170 while the drive shaft member 150 remains stationary. The breakaway torque can cause the plurality of fingers 230a-d to deform and move past anti-rotation members 270.

Figure 12A:
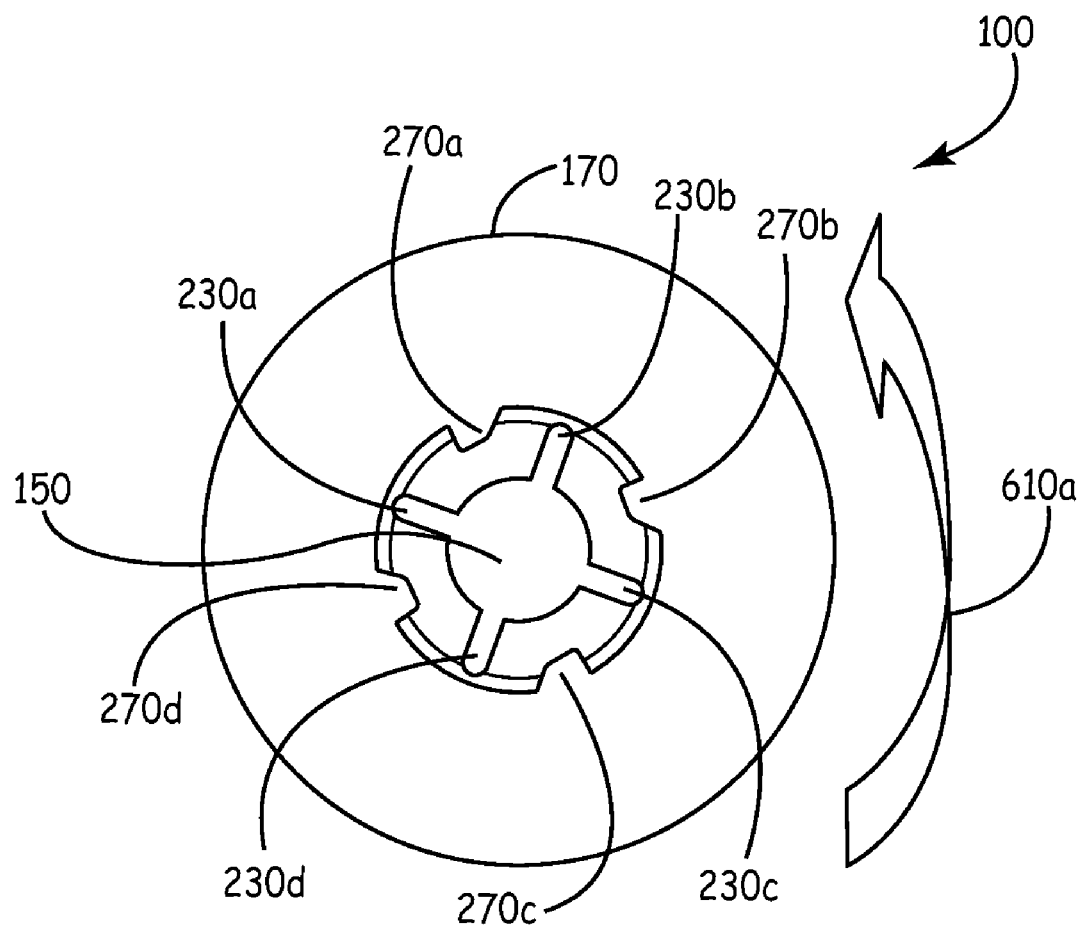
FIG. 12A depicts a top schematic view of an exemplary torque wrench in which the handle is rotated counterclockwise to disengage flexible fingers from the anti-rotation members in the handle.
Figure 12B:
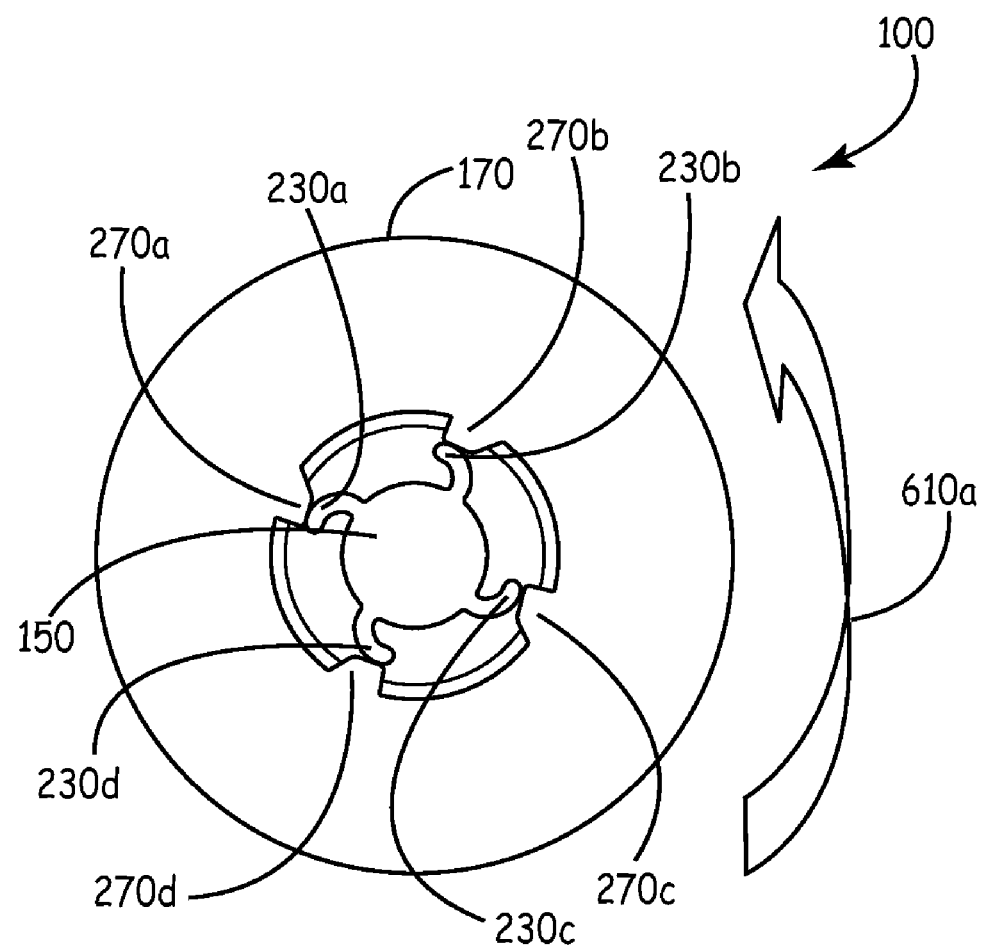
FIG. 12B depicts a top schematic view of the exemplary torque wrench depicted in FIG. 12A in which the handle is again rotated counterclockwise such that a breakaway torque is applied and flexible fingers begin to rotate past the anti-rotation members in the handle.

FIGS. 12A-13B depict additional finger 230 geometries that can be implemented. For example, FIG. 12A shows fingers 230 in a relaxed position. Each finger is depicted as being in a substantially cylindrical shape. In this embodiment, fingers 230 are perpendicular or substantially perpendicular to drive shaft axis 235 of drive shaft member 150. Rotating the handle 170 in the counterclockwise direction 610A relative to the drive shaft member 150 with a torque that is at least as large as the counterclockwise breakaway torque causes the fingers 230 to deform such that the fingers 230 can rotate past the anti-rotation members 270 as shown in FIG. 12B. In this embodiment, the fingers 230 flex up to about 90 degrees as the fingers 230 rotate past the anti-rotation members 270.

Figure 13A:
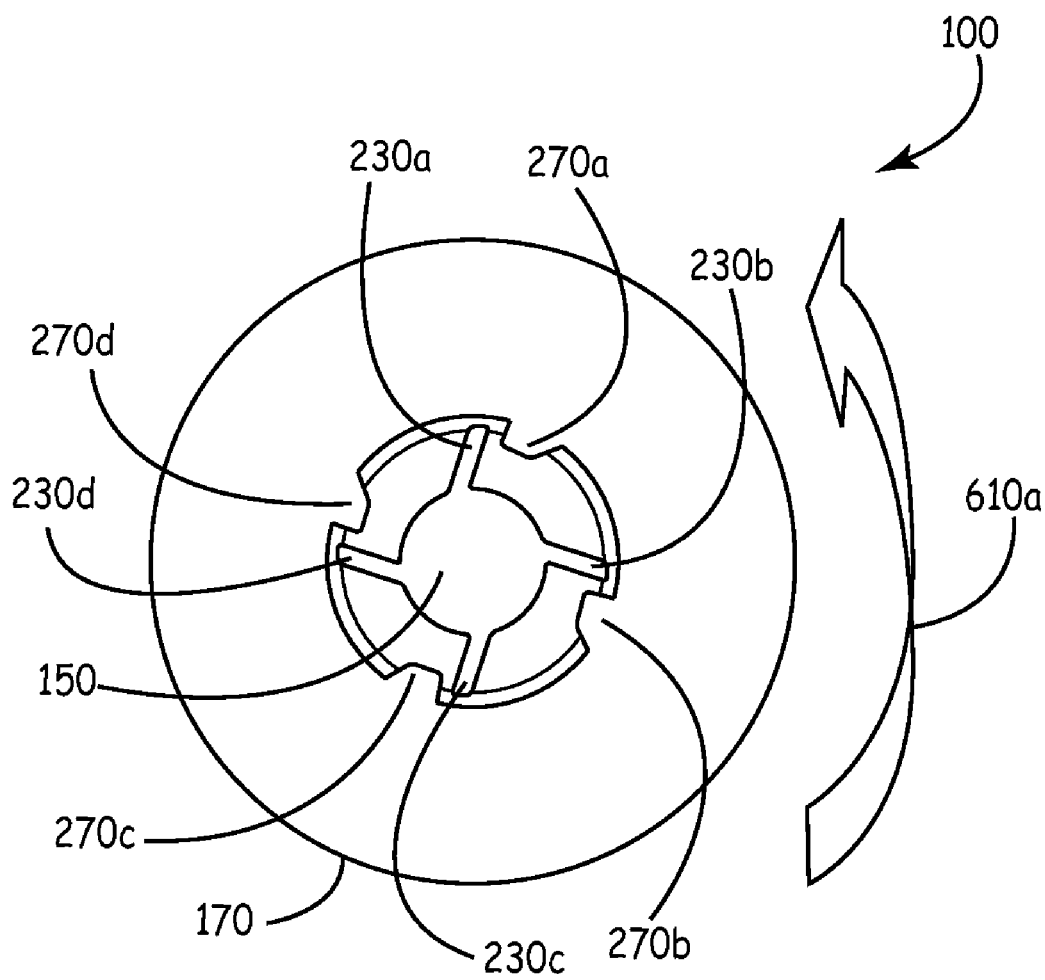
FIG. 13A depicts a top schematic view of an exemplary torque wrench in which the handle is rotated counterclockwise to disengage flexible fingers from the anti-rotation members in the handle.
Figure 13B:
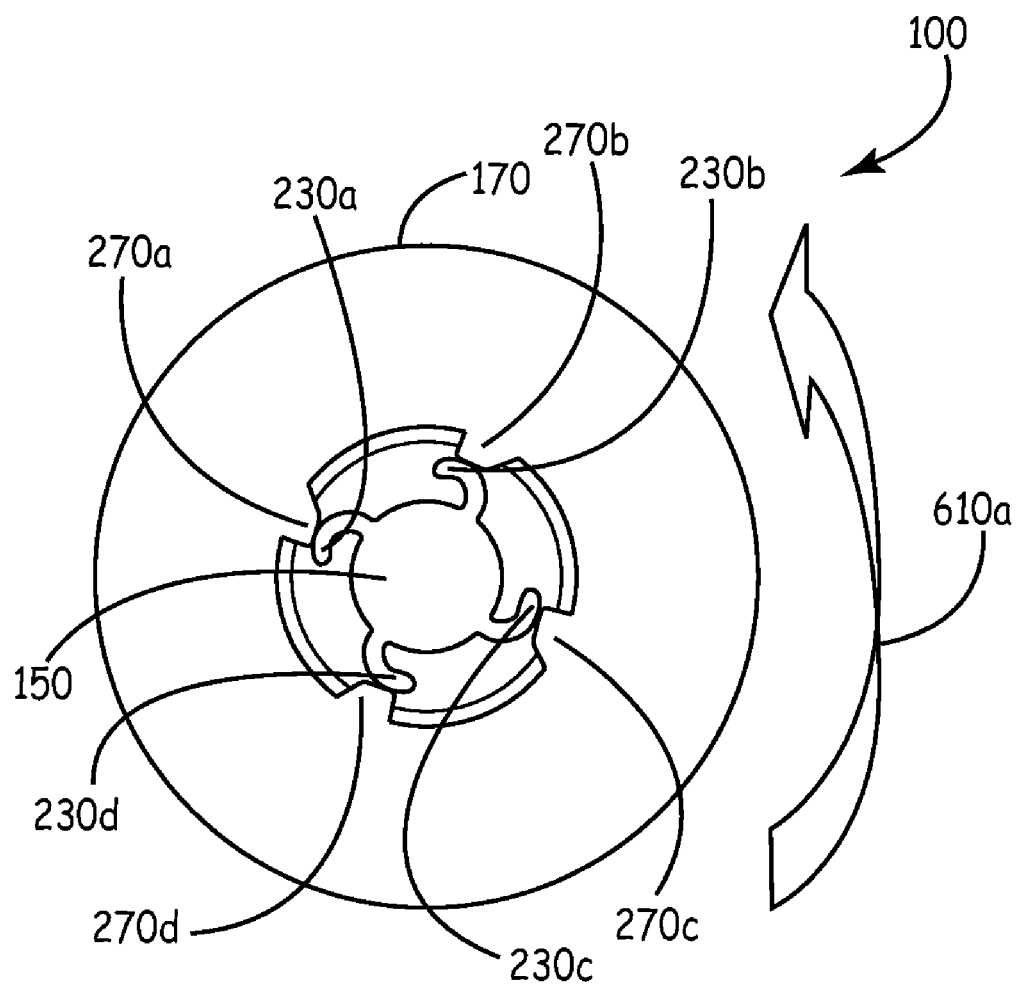
FIG. 13B depicts a top schematic view of the exemplary torque wrench depicted in FIG. 13A in which the handle is again rotated counterclockwise such that a breakaway torque is applied and flexible fingers begin to rotate past the anti-rotation members in the handle.

FIG. 13A shows yet another embodiment with fingers 230 in the relaxed position. In this embodiment, the fingers 230 extend from the drive shaft member 150 at an angle compared to a direction perpendicular to the drive shaft axis 235 yet the fingers 230 still extend in a substantially perpendicular direction relative to the drive shaft member 150. In some embodiments, the angle relative to a direction perpendicular to the drive shaft axis 235 at which the fingers 230 extend from the drive shaft member 150 is between about 0 and 25 degrees. In other embodiments, the angle is between about 0 and 45 degrees. In still yet other embodiments, the angle is between 0 and 90 degrees. Rotating the handle 170 in the counterclockwise direction 610A relative to the drive shaft member 150 with a torque that is at least as large as the counterclockwise breakaway torque causes the fingers 230 to deform such that the fingers 230 can rotate past the anti-rotation members 270 as shown in FIG. 13B. In this embodiment, the fingers 230 can flex from a relaxed position to a stressed position up to about 180 degrees as the fingers 230 rotate past the anti-rotation members 270.

FIGS. 14-30 depict various exemplary torque wrench embodiments to illustrate the wide range of ways in which flexible fingers 230 can be used to create torque limiting mechanisms. Skilled artisans will recognize the similarities between the depicted torque wrench embodiments which share common trait(s) including the lack of a helical spring to limit the torque transferred between the handle 170 and the drive shaft member 150.

Figure 14:
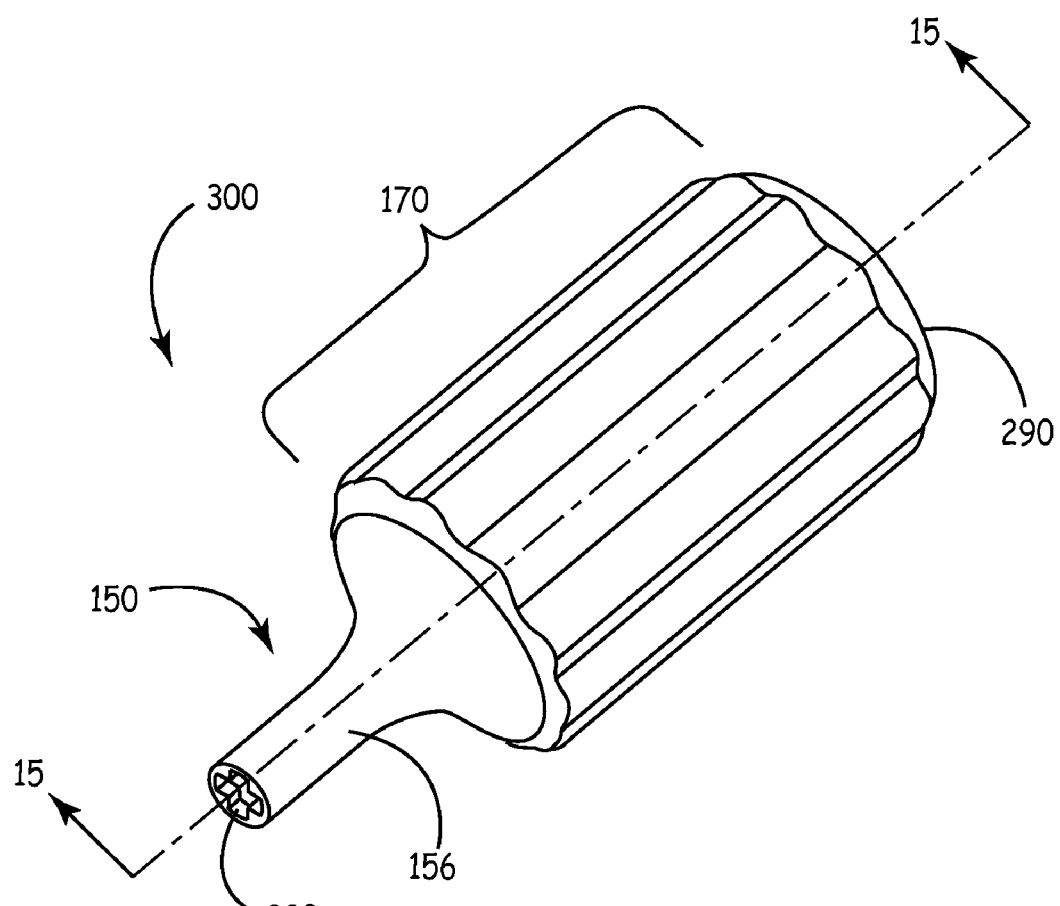
FIG. 14 is a schematic exterior view of another exemplary torque wrench.
Figure 15:
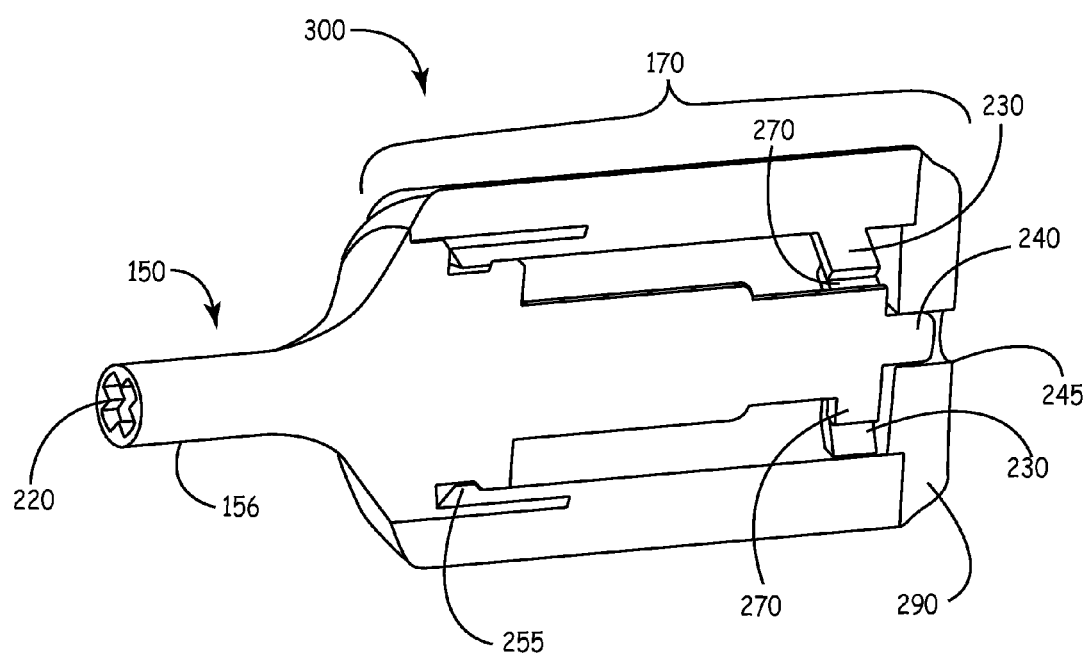
FIG. 15 depicts a cutaway view of the exemplary torque wrench from FIG. 14 taken along lines 15-15.
Figure 16:
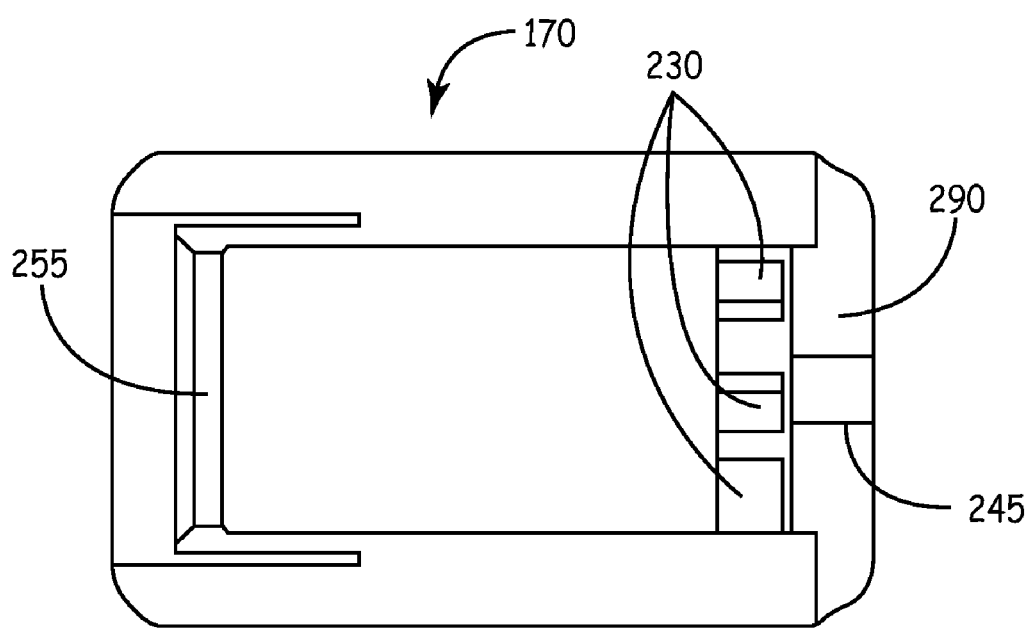
FIG. 16 is a schematic side view of the exemplary handle of FIG. 14 in which the handle is cutaway along lines 15-15.

FIGS. 14-16 depict an exemplary torque wrench 300 with flexible fingers 230 to limit the maximum torque that can be transferred between the handle 170 and the drive shaft member 150. In this embodiment, the flexible fingers 230 extend from the handle 170 and substantially point towards the drive shaft axis 235 while a plurality of anti-rotation members 270 or protrusions are formed on the outer surface of the drive shaft member 150. FIG. 15 shows a cutaway view of the exemplary torque wrench 300 from FIG. 14 taken along lines 15-15. The anti-rotation members 270, previously described, can be positioned on the drive shaft member 150 such that the anti-rotation members 270 are able to engage or contact the fingers 230. While fingers 230 are depicted as being located near the distal end of the handle 170, skilled artisans appreciate that fingers 230 can be located anywhere on interior portion of the handle 170 that faces the drive shaft member 150. In another embodiment, the fingers 230 are located near the proximal end of the handle 170. In some embodiments, the fingers 230 are placed 0 to 0.5 inches from the distal end of the handle 170. In yet other embodiments, the fingers 230 are placed anywhere from about 0 to about 1.5 inch from the distal end of the handle 170.

In one or more embodiments, the anti-rotation members 270 deform less than the fingers 230. In another embodiment, the anti-rotation members 270 do not deform more than ten percent of the rotational deformation of the fingers 230. In yet another embodiment, the fingers 230 and the anti-rotation members 270 deform about equally.

The combined deformation of each connecting pair, which is one finger 230 and one anti-rotation member 270 that are touching or engaged, should be sufficient to allow the handle 170 to rotate relative to the drive shaft member 150 more than 360 degrees when a torque at least as large as the breakaway torque is applied between the handle 170 and the drive shaft member 150. The combined deformation of each connecting pair should not be sufficient to allow the handle 170 to rotate relative to the drive shaft member 150 more than 360 degrees when a torque less than the breakaway torque is applied between the handle 170 and the drive shaft member 150. For example, a finger 230 might deform 70 degrees and an anti-rotation member 270 that is engaged with the finger 230 might deform 20 degrees. The deformation of the finger 230 without the deformation of the anti-rotation member 270 may be insufficient to allow the finger 230 to rotate past the anti-rotation member 270 when a breakaway torque is applied. Yet, the deformation of the finger 230 combined with the deformation of the anti-rotation member 270 can be sufficient to allow the finger 230 to rotate past the anti-rotation member 270 when a breakaway torque is applied.

Deformation of the fingers 230 and/or the deformation of the anti-rotation members 270 due to an applied torque in at least one rotational direction should not damage the fingers 230 and/or the anti-rotation members 270. Damage may occur when the breakaway torque in a given rotational direction changes by more than 50 percent from one cycle to the next cycle. A cycle involves increasing the torque between the handle 170 and the drive shaft member 150 until the handle 170 moves more than 360 degrees but less than 720 degrees relative to the drive shaft member 150.

In one or more embodiments, applying the breakaway torque during one cycle in the clockwise direction typically does not change the breakaway torque more than 50 percent in the next clockwise cycle, but exceeding the breakaway torque in the counterclockwise direction will change the breakaway torque more than 50 percent in the next cycle. For example, a torque wrench may not be damaged by clockwise cycles but can be damaged by counterclockwise cycles. In another example, a torque wrench may not be damaged by counterclockwise cycles but can be damaged by clockwise cycles.

In one or more embodiments, fingers 230 are located near a cap 290 disposed at the distal end of the torque wrench 100. Cap 290 simplifies the moldability of the rest of the handle 170 by allowing adequate mold tool access to the fingers 230. The torque wrench 300 in FIGS. 14-16 is assembled by first snapping or bonding the cap 290 onto distal end of the handle 170. Thereafter, the drive shaft member 150 is pressed into the proximal end of the handle 170 until the snap protrusion 255 snaps into the handle 170. FIG. 16 depicts a cutaway view of the handle 170 from FIG. 14 taken along lines 15-15.

FIGS. 17-22 depict a torque wrench 400 in which the flexible fingers 230 extend substantially parallel to the drive shaft axis 235. More particularly, the flexible fingers 230 are attached to or extend from the handle 170. The fingers 230 are located near the proximal end of the handle 170. In one or more embodiments, flexible fingers 230 can be used to create a torque wrench that does not use a helical spring to limit the torque transferred from the handle 170 to the drive shaft member 150.

Figure 17:
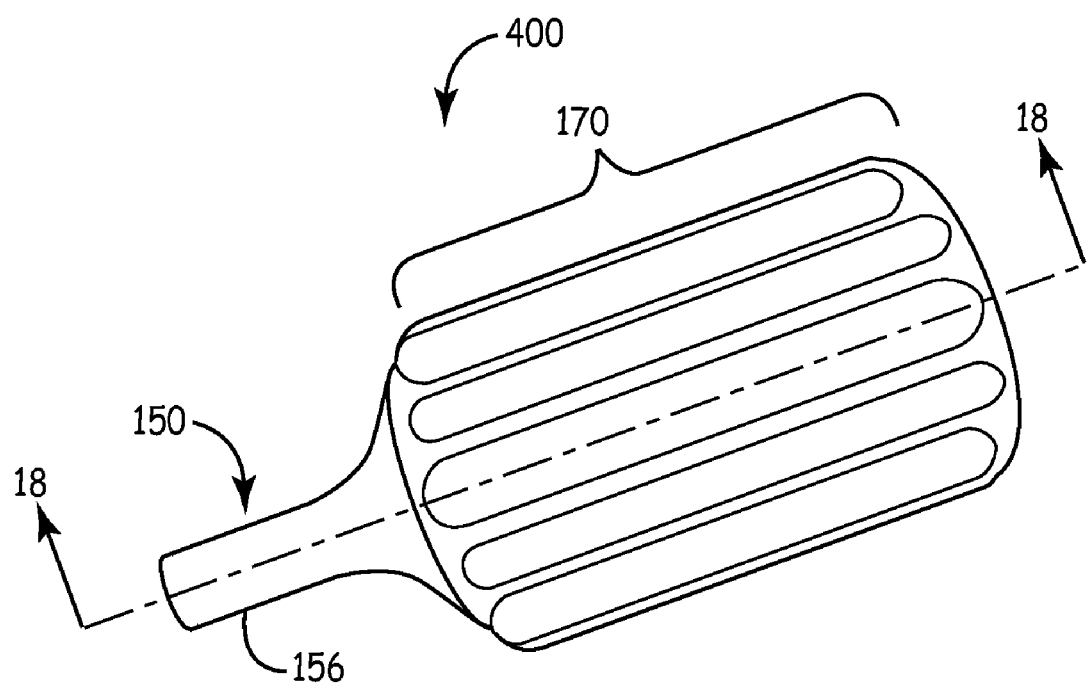
FIG. 17 is a schematic exterior view of another exemplary torque wrench.
Figure 18:
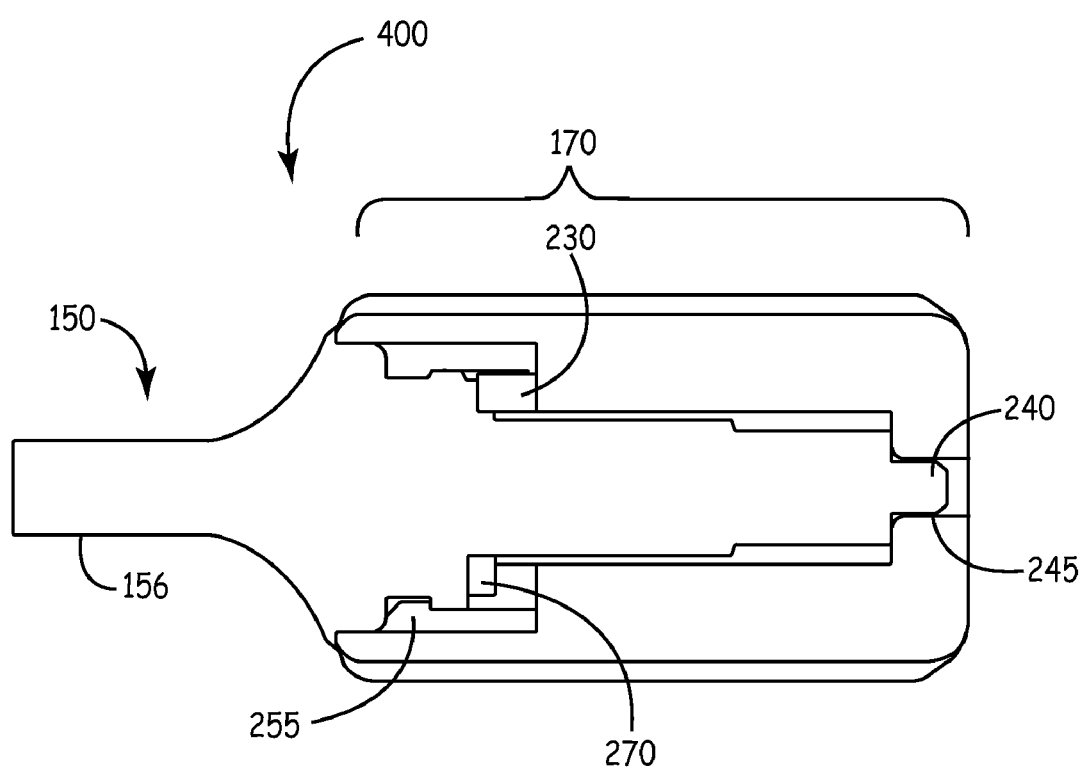
FIG. 18 depicts a cutaway view of the exemplary torque wrench from FIG. 17 taken along lines 18-18.

FIG. 18 shows a cutaway view of the exemplary torque wrench 100 from FIG. 17 taken along lines 18-18. In this embodiment, a plurality of anti-rotation members 270 or protrusions are formed on the outer surface of the drive shaft member 150. The anti-rotation members 270 are positioned on the drive shaft member 150 such that the anti-rotation members 270 are able to engage or come in contact with the fingers 230. In this embodiment, fingers 230 are located on the handle 170 and extend parallel or substantially parallel to the drive shaft axis 235. The fingers 230 can be located anywhere on an interior portion of the handle 170 that faces the drive shaft member 150. In this embodiment, the fingers 230 are located near the proximal end of the handle 170. In another embodiment, the fingers 230 are located near the distal end of the handle 170.

In this embodiment, the anti-rotation members 270 deform less than the fingers 230. The interaction between the anti-rotation members 270 and the fingers 230 prevent the handle from rotating more than 360 degrees relative to the drive shaft member 150 unless a torque at least as large as the breakaway torque is applied between the handle 170 and the drive shaft member 150. In this embodiment, applying the breakaway torque does not damage the fingers 230 and/or the anti-rotation members 270.

Figure 19:
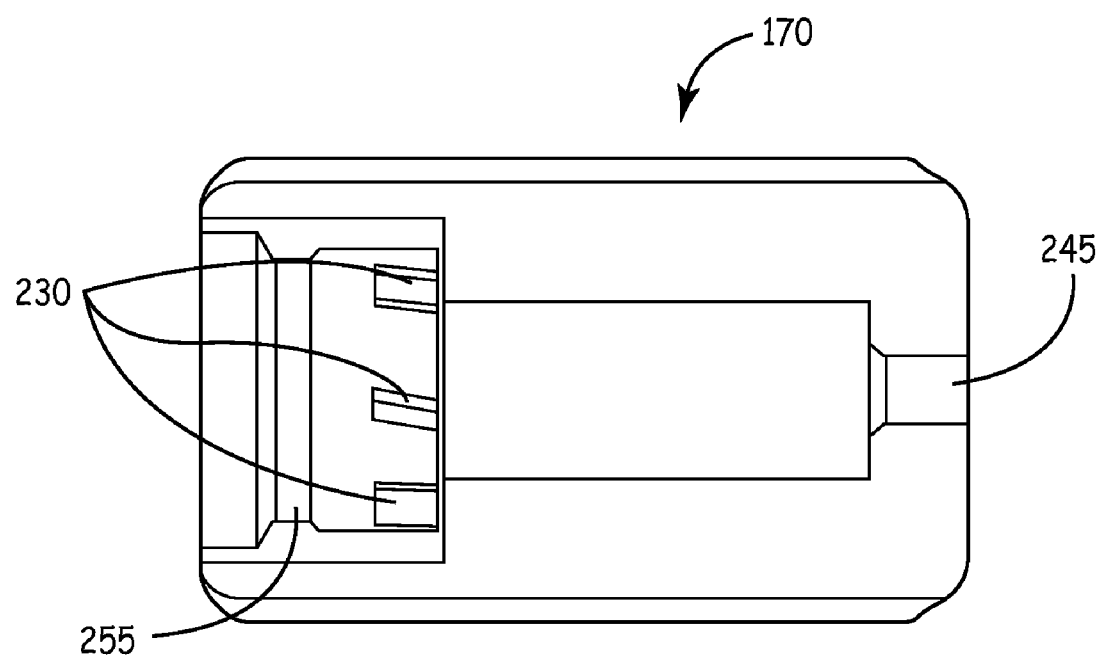
FIG. 19 is a schematic side view of the exemplary handle of FIG. 17 in which the handle is cutaway along lines 18-18.
Figure 20:
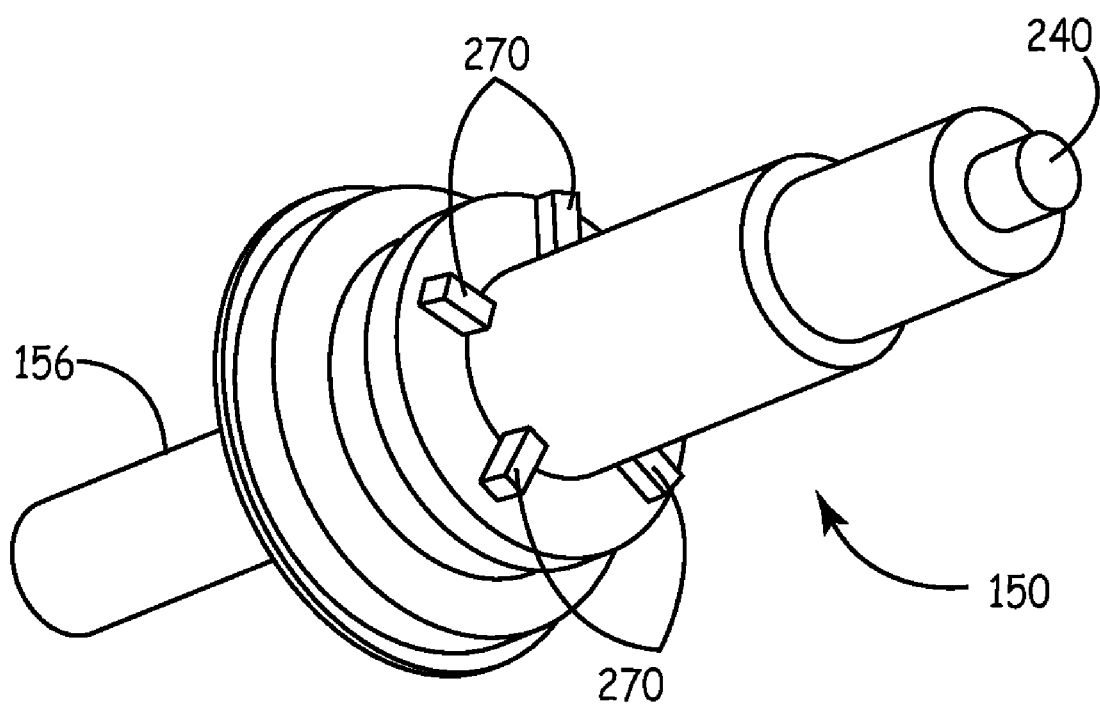
FIG. 20 is a schematic exterior view of the drive shaft member from the torque wrench depicted in FIG. 17.

The torque wrench in FIGS. 17-20 is assembled by pressing the drive shaft member 150 into the proximal end of the handle 170 until the snap protrusion 255 snaps into the handle 170. FIG. 19 depicts a cutaway view of the handle 170 from FIG. 17 taken along lines 18-18. Fingers 230 in FIG. 19 also lack a helical spring. In some embodiments, the fingers 230 and/or the anti-rotation members 270 comprise or consist of a polymeric material.

Figure 21:
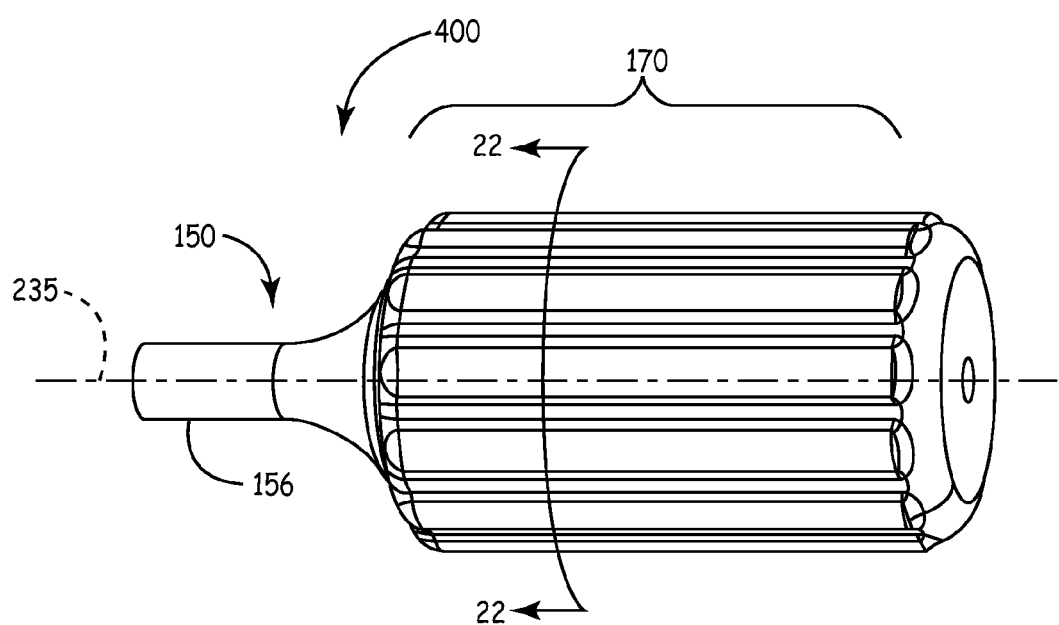
FIG. 21 is a schematic exterior view of the torque wrench depicted in FIG. 17.
Figure 22:
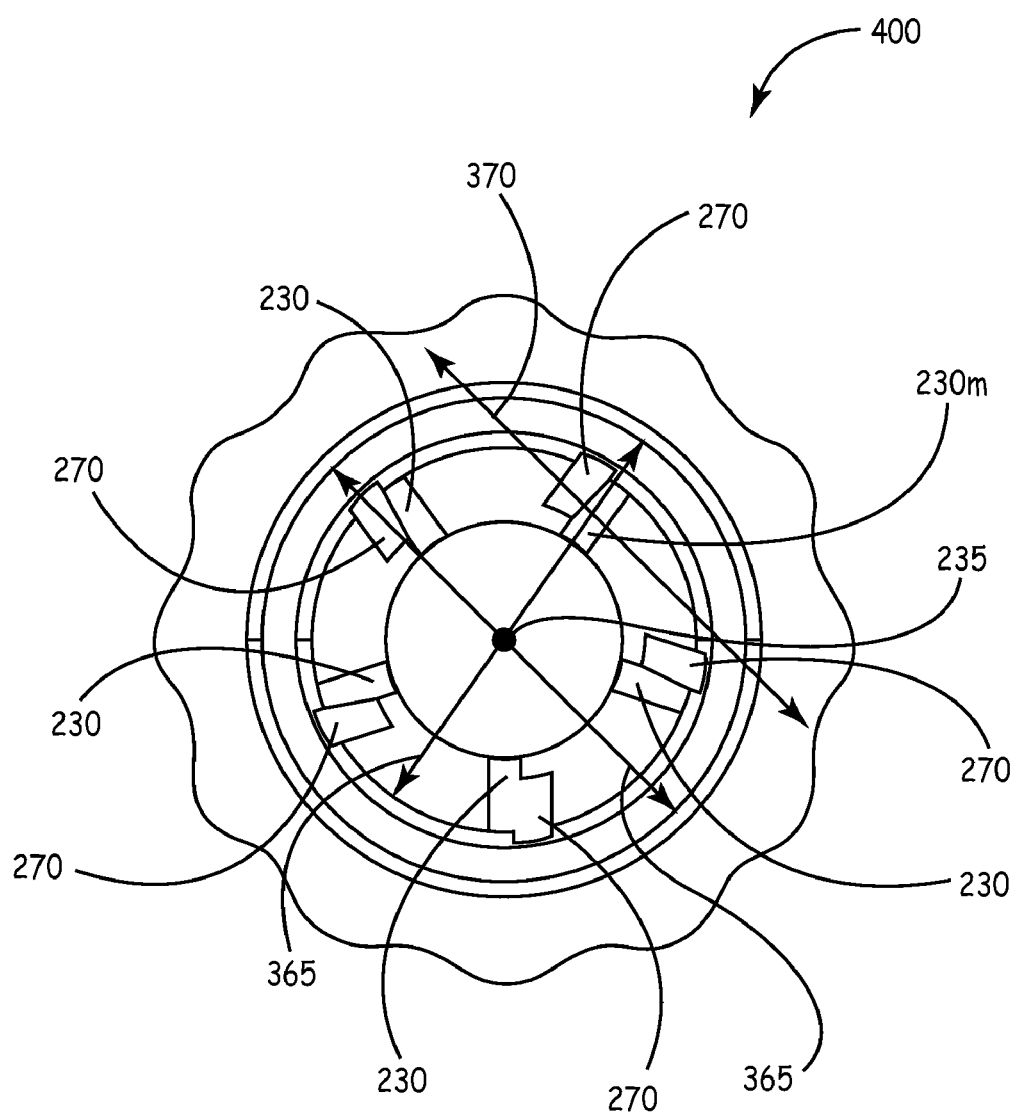
FIG. 22 depicts a cutaway view of the exemplary torque wrench from FIG. 21 taken along lines 22-22.

FIG. 22 shows a cutaway view of the exemplary torque wrench 400 from FIG. 21 taken along lines 22-22. FIG. 22 depicts exemplary perpendicular lines 365 that are perpendicular to the drive shaft axis 235. Exemplary torsional force direction 370, perpendicular to the exemplary perpendicular lines 365, substantially acts on finger 230m. Torsion is the moment arm multiplied by the applied torsional force. In one or more embodiments, a finger 230 that is substantially aligned with the drive shaft axis 235 deforms substantially along the torsional force direction 370 plus or minus 45 degrees of the torsional force that acts on the finger 230.

Figure 23:
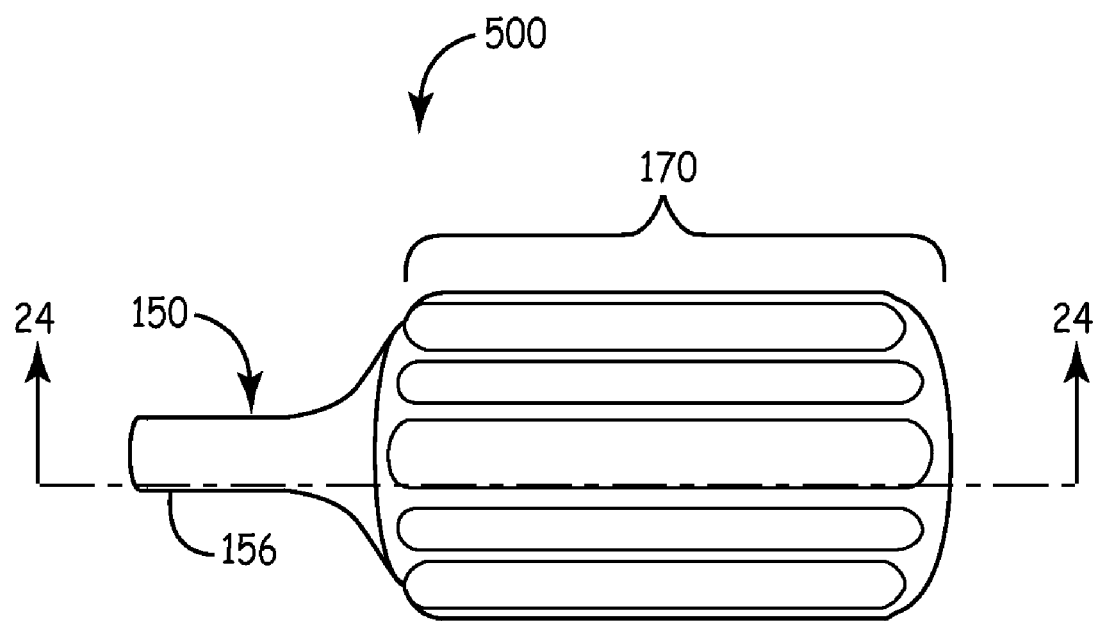
FIG. 23 is a schematic exterior view of another exemplary torque wrench.
Figure 24:
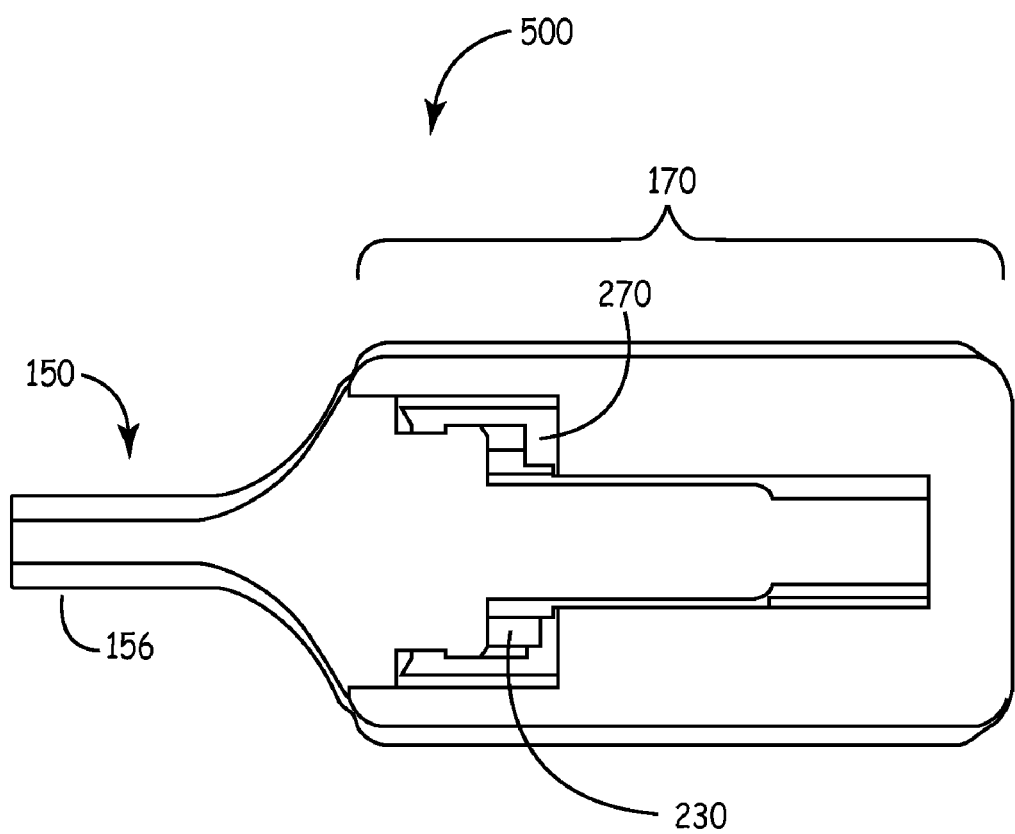
FIG. 24 depicts a cutaway view of the exemplary torque wrench from FIG. 23 taken along lines 24-24.
Figure 25:
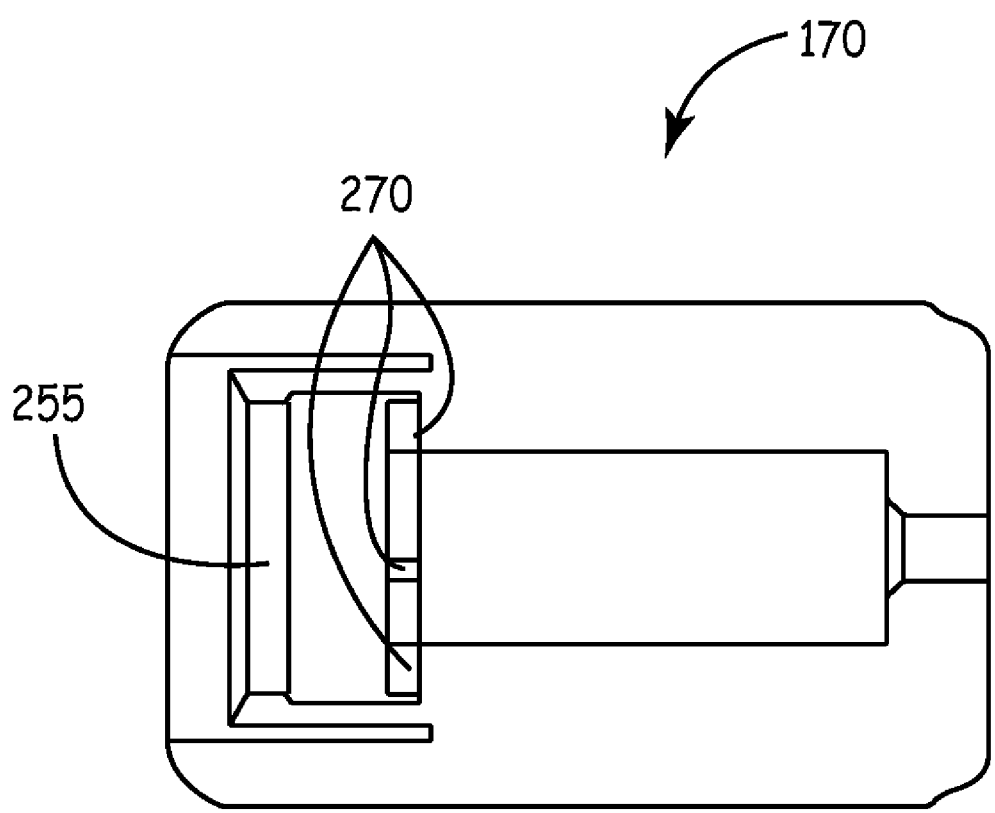
FIG. 25 is a schematic side view of the exemplary handle of FIG. 23 in which the handle is cutaway along lines 24-24.

FIGS. 23-24 depict a torque wrench 500 in which the flexible fingers 230 are attached to the drive shaft member 150 and the fingers 230 substantially extend parallel to the drive shaft axis 235. FIG. 24 shows a cutaway view of the exemplary torque wrench 500 from FIG. 13 taken along lines 24-24. In this embodiment, a plurality of anti-rotation members 270 or protrusions are formed on an interior surface of the handle 170. FIG. 25 depicts the anti-rotation members 270 on the interior surface of the handle. The anti-rotation members 270 are positioned on the handle 170 such that the anti-rotation members 270 are able to engage or come in contact with the fingers 230, which in this embodiment, are located on the drive shaft member 150 and extend substantially parallel to the drive shaft axis 235. The fingers 230 can be located anywhere on the drive shaft member 150 that faces the handle 170. In this embodiment, the fingers 230 are located on the drive shaft member 150 near the proximal end of the handle 170.

Figure 26:
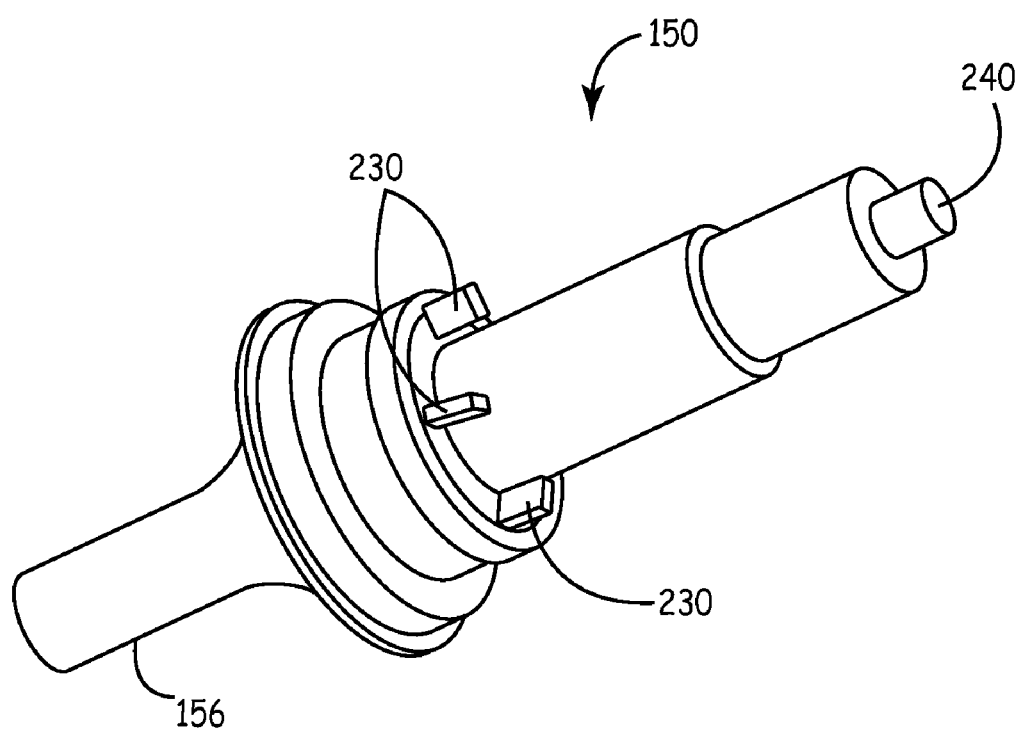
FIG. 26 is a schematic exterior view of the drive shaft member from the torque wrench depicted in FIG. 23.

In this embodiment, the anti-rotation members 270 do not deform. The fingers 230 do not deform sufficiently to allow the drive shaft member 150 to rotate relative to the handle 170 unless a torque at least as large as the breakaway torque is applied between the handle 170 and the drive shaft member 150. FIG. 26 depicts the fingers 230 which are long and slender with rectangular surfaces. The fingers 230 and the anti-rotation members are not damaged when the breakaway torque is applied between the handle 170 and the drive shaft member 150.

The torque wrench in FIGS. 23-26 can be assembled by pressing the drive shaft member 150 into the proximal end of the handle 170 until the snap protrusion 255 snaps into the handle 170. The fingers 230 in FIG. 26 lack a helical spring. In some embodiments, the fingers 230 and/or the anti-rotation members 270 comprise or consist of a polymeric material. In the torque wrench embodiment shown in FIGS. 23-26, the handle 170 is plastic and the drive shaft member 150 is metal.

The drive shaft member 150 in this embodiment can be formed by electrical discharge machining. A similar embodiment can be manufactured by stamping and forming the fingers 230 and then pressing the fingers 230 into a molded body wherein the molded body and the fingers 230 comprise the drive shaft member 150. More specifically, a ring can be stamped or cut from a flat sheet of metal that is about approximately 0.035 inches thick. Next, the fingers 230 can be manufactured by stamping or cutting multiple holes such as U-shaped holes into the metal sheet. The suspended metal sections formed by stamping or cutting multiple U-shaped holes are then bent or formed such that each suspended metal section extends at an angle of about 45 to 90 degrees from the plane in which the majority of the metal ring resides. The suspended metal sections are fingers 230 and the ring is attached to the rest of the drive shaft member 150.

Figure 27:
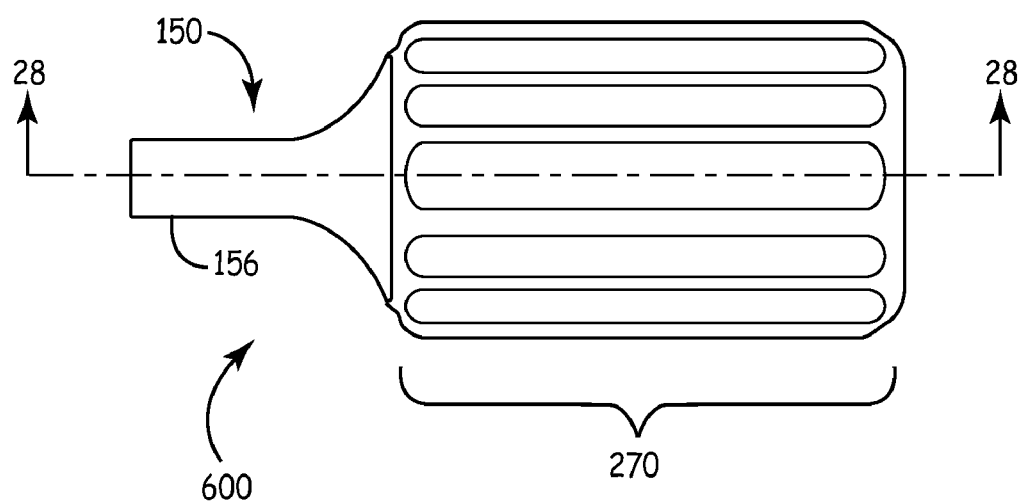
FIG. 27 is a schematic exterior view of another exemplary torque wrench.
Figure 28:
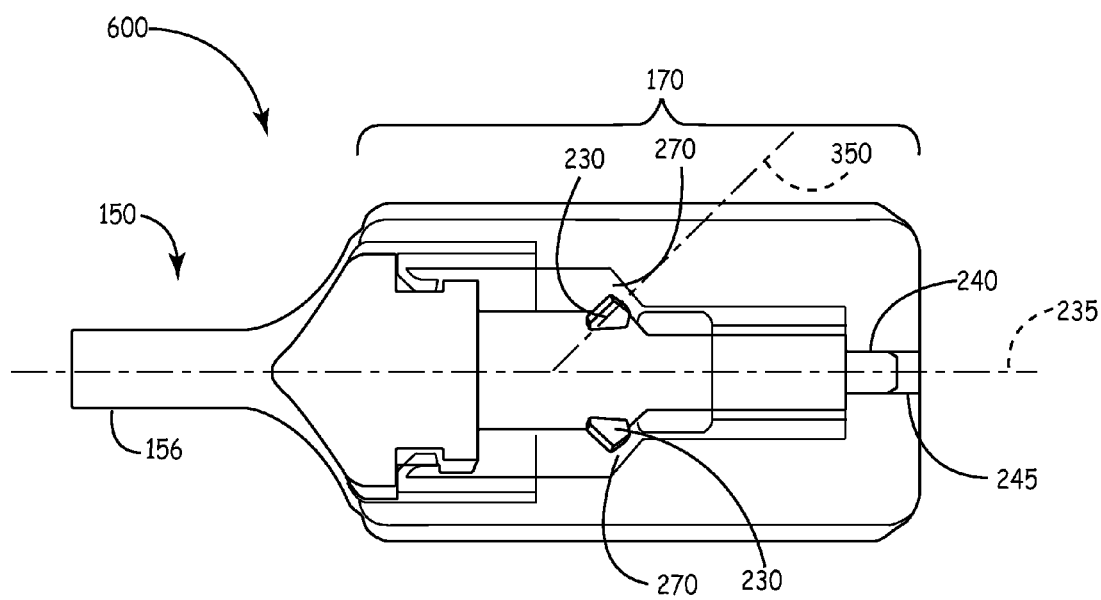
FIG. 28 depicts a cutaway view of the exemplary torque wrench from FIG. 27 taken along lines 28-28.

FIG. 27 depicts a torque wrench 600 in which the flexible fingers 230 extend at an angle relative to the drive shaft axis 235. FIG. 28 shows a cutaway view of the exemplary torque wrench 600 from FIG. 27 taken along lines 28-28. In this embodiment, the fingers 235 are attached to the drive shaft member 150 and the fingers 230 extend at an angle relative to the drive shaft axis 235. In another embodiment, the fingers 230 are attached to the handle 170 and extend at an angle relative to the drive shaft axis 235.

Figure 29:
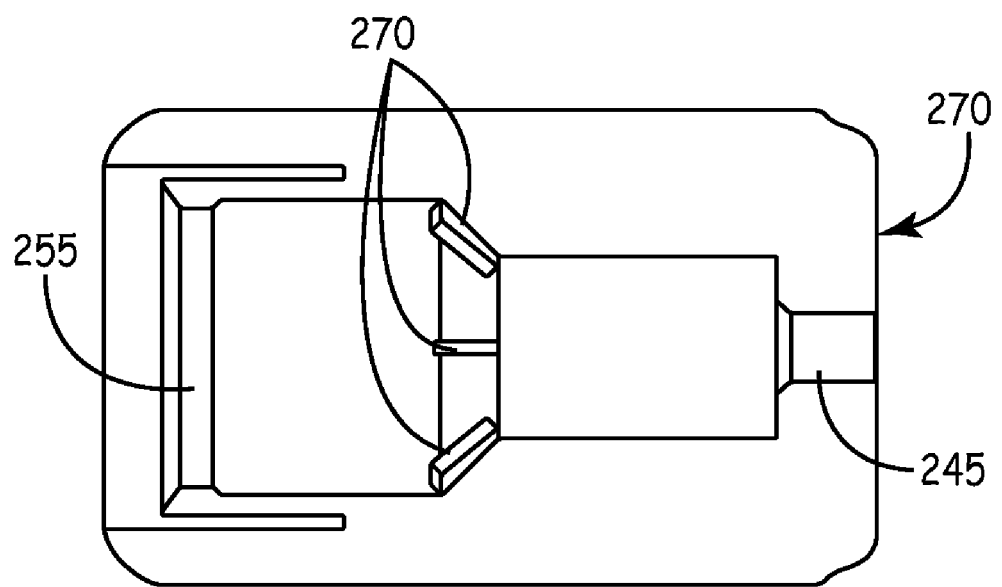
FIG. 29 is a schematic side view of the exemplary handle of FIG. 27 in which the handle is cutaway along lines 28-28.
Figure 30:
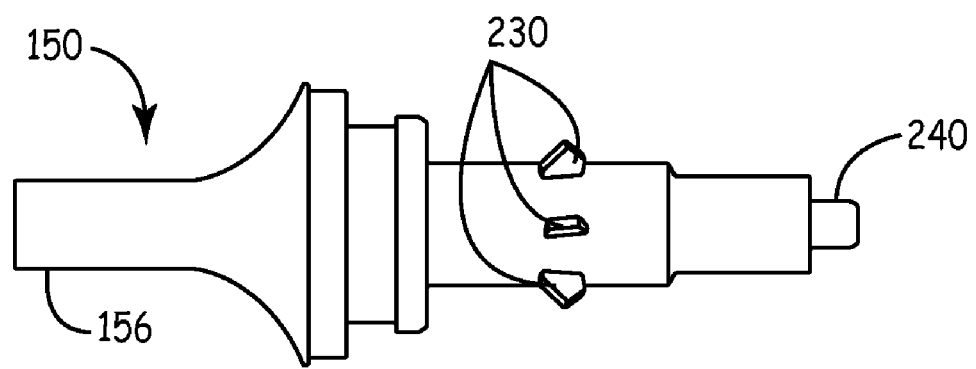
FIG. 30 is a schematic exterior view of the drive shaft member from the torque wrench depicted in FIG. 27.

FIG. 29 shows a cutaway view of the handle 170 from FIG. 27 taken along lines 28-28. In this embodiment, a plurality of anti-rotation members 270 or protrusions are formed on an interior surface of the handle 170. The anti-rotation members 270 are positioned on the handle 170 such that the anti-rotation members 270 are able to engage or come in contact with the fingers 230, which in this embodiment, are located on the drive shaft member 150 and extend at an angle relative to the drive shaft axis 235. FIG. 28 shows the finger extension angle 350, which depicts the angle at which the fingers 230 extend from the drive shaft member 150 relative to the drive shaft axis 235 in this embodiment. The finger extension angle can be 0 to 180 degrees from the drive shaft member 150 relative to the drive shaft axis 235. The fingers 230 can be located anywhere on the drive shaft member 150 that faces the handle 170. In this embodiment, the fingers 230 are located on the drive shaft member 150 near the middle of the handle 170. In another embodiment, the fingers 230 are located near the distal end of the drive shaft member 150. In another embodiment, the fingers 230 are located near the proximal end of the drive shaft member 150.

The anti-rotation members 270 do not allow the fingers 230 to rotate past the anti-rotation members 270 unless a torque at least as large as the breakaway torque is applied between the handle 170 and the drive shaft member 150. When a torque at least as large as the breakaway torque is applied between the handle 170 and the drive shaft member 150, the fingers 230 elastically deform to enable the fingers 230 to rotate past the anti-rotation members 270. The deformation caused by the fingers 230 rotating past the anti-rotation members 270 does not damage the fingers 230 and/or the anti-rotation members 270.

Torque wrench 600 in FIGS. 27-30 is assembled by pressing the drive shaft member 150 into the proximal end of the handle 170 until the snap protrusion 255 snaps into the handle 170. The fingers 230 in FIG. 26 lack a helical spring. In some embodiments, the fingers 230 and/or the anti-rotation members 270 consist of a polymeric material. In some embodiments, the fingers 230 and/or the anti-rotation members 270 consist of a metal material. Metal fingers 230 can be formed by processes such as machining, stamping and forming or other suitable methods.

Figure 31:
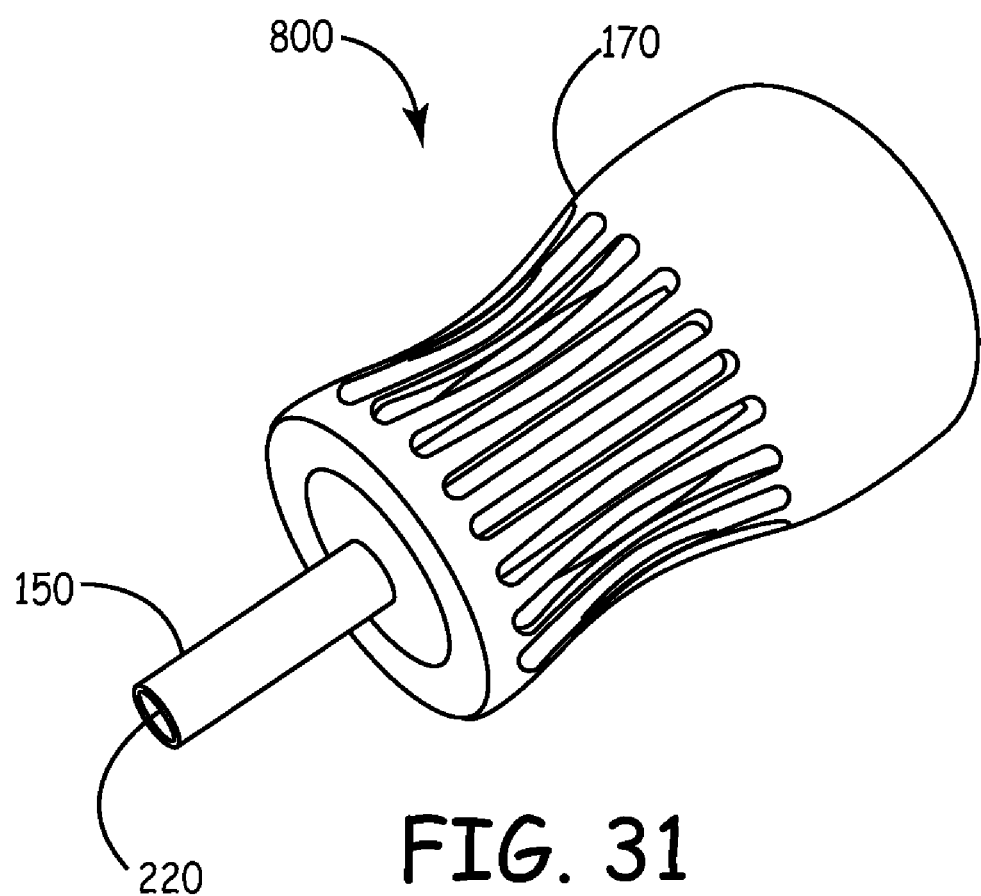
FIG. 31 is a schematic exterior view of an exemplary torque wrench.

FIG. 31 is a flow diagram that depicts formation of an exemplary torque wrench. At block 300, a first component is provided. The first component can be provided by being formed through introduction of one or more polymers into a mold that undergoes a molding process. The first component can have a bore there through. For example, the first component can be a cylindrical body with a bore centrally located through the cylindrical body. Additionally, the first component can be a handle or other suitable object. At block 320, a second component is provided. The second component can be provided or formed through introduction of one or more polymers into a mold that undergoes a molding process. At block 330, the second component is coupled to the first component. The second component can include a middle portion that has first and second ends. A drive shaft can extend from the first end. Additionally, a plurality of fingers extend from an exterior surface of the second end. The second component can be received in the bore of the first component, such that the drive shaft partially extends outside the first end of the first component and the plurality of fingers interdigitate with the anti-rotation members of the first component. The second component can be a drive shaft member or other suitable object.

Although the present disclosure has been described in considerable detail with reference to certain disclosed embodiments, the disclosed embodiments are presented for purposes of illustration and not limitation and other embodiments of the disclosure are possible. For example, in one or more other embodiments, torque wrench 100 is solely formed of handle 170 and drive shaft member 150, as described herein. It will be appreciated that various changes, adaptations, and modifications may be made without departing from the spirit of the disclosure and the scope of the appended claims. In one or more embodiments, breakaway torque in the clockwise direction can be different from the breakaway torque in the counterclockwise direction due, at least in part, to the shape of the flexible fingers 230 and/or the shape of the anti-rotation members 270. In one or more embodiments, the flexible fingers 230 are symmetrical in the clockwise direction and counterclockwise direction such that the breakaway torque in the clockwise direction is about equal to the breakaway torque in the counterclockwise direction. In another embodiment, the flexible fingers 230 are attached to or part of the handle 170. In this embodiment, the flexible fingers generally extend towards the drive shaft member 150 and the anti-rotation features are located on the drive shaft member 150. In yet another embodiment, the flexible fingers 230 are approximately aligned with the drive shaft axis 235 and generally deform in a direction aligned with the direction of the torsion force rather than deform in a direction generally perpendicular to the drive shaft axis 235. In some embodiments, the fingers 230 and/or the anti-rotation members 270 comprise or consist of a polymeric material. Skilled artisans appreciate that the sizes of components can be modified to implement features of the embodiment(s) described herein.

FIGS. 31 through 35 depict yet another embodiment of a torque wrench 800. Torque wrench 800 consists of, or, comprises a drive shaft member 150, a handle 170, and a compressible member 310. In this embodiment, drive shaft member 150, depicted in FIGS. 34-35, includes a drive shaft end 158, a middle portion 152, finger end 154. Handle 170 is the same as previously described except, in this embodiment, handle 170 also includes a bore area 312 which allows sufficient space to house compressible member 310 between handle 170 and drive shaft member 150. Bore area 312 has an inner diameter that can range from about 0.2 inches to about 0.4 inches. Bore area 312 can also extend in length along the drive shaft axis from about 0.1 inches to about 0.25 inches. In another embodiment, the inner diameter for area 312 can be 0.1 inches to 0.5 inches. In yet another embodiment, inner diameter for area 312 can be 0.05 inches to about 0.70 inches. In still yet another embodiment, inner diameter for area 312 can be 0.01 inches to about 1.5 inches. Additionally, area 312 can extend a distance of about 0.05 inches to about 0.5 inches. In another embodiment, area 312 can extend a distance of about 0.02 inches to about 1.5 inches.

In one or more embodiments, compressible member 310 surrounds a middle portion 152 of drive shaft member 150; however, compressible member 310 can be placed in different locations along drive shaft member 150. An exemplary compressible member 310 can include a spring, a wave washer, a cantiever beam, or other suitable structures.

Figure 32A:
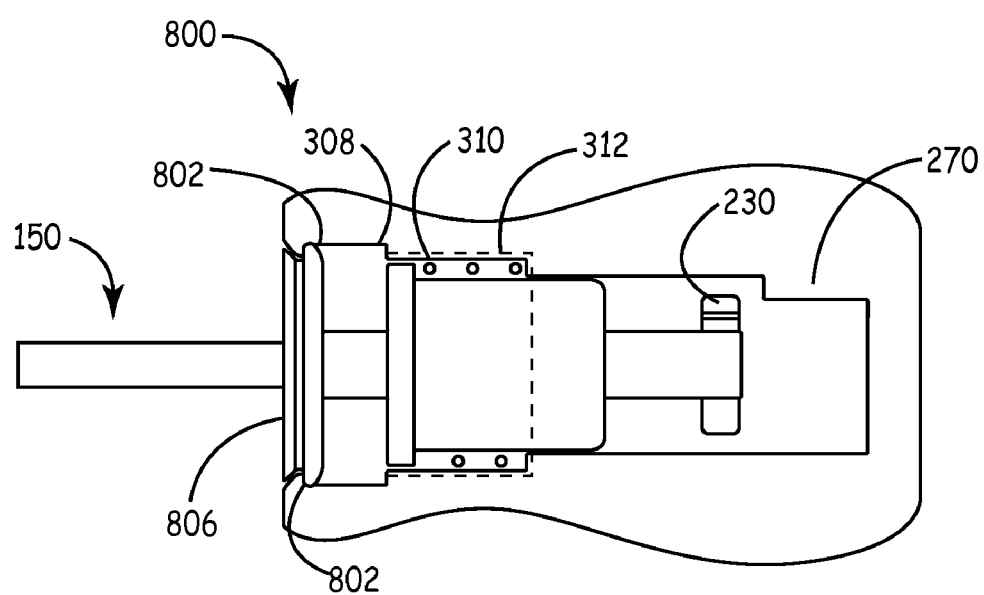
FIG. 32A is a schematic side view of the exemplary torque wrench of FIG. 31 in which a compression member is expanded around a drive shaft member.

Compressible member 310, either free-standing or connected to handle 170 and/or middle portion 152, is configured to move drive shaft member 150 relative to handle 170 along drive shaft axis 235. The compressible member 310 is movable along the drive shaft member 150 between a first configuration and a second configuration. A first configuration occurs when the compressible member 310 is expanded or not compressed, as depicted in FIG. 32A. In this configuration, torque wrench 800 is not being forced against a connector 200; therefore, the compressible member 310 is in a relaxed or expanded position. An expanded position of compressible member 310 involves greater space between, for example, each filar of a coil as compared to a compressible member 310 that is compressed. When torque wrench 800 is not engaged or pressed against connector 200, plurality of fingers 230 are disengaged from anti-rotation members 270; therefore, handle 170 can spin freely or relatively freely relative to drive shaft member 150.

Figure 32B:
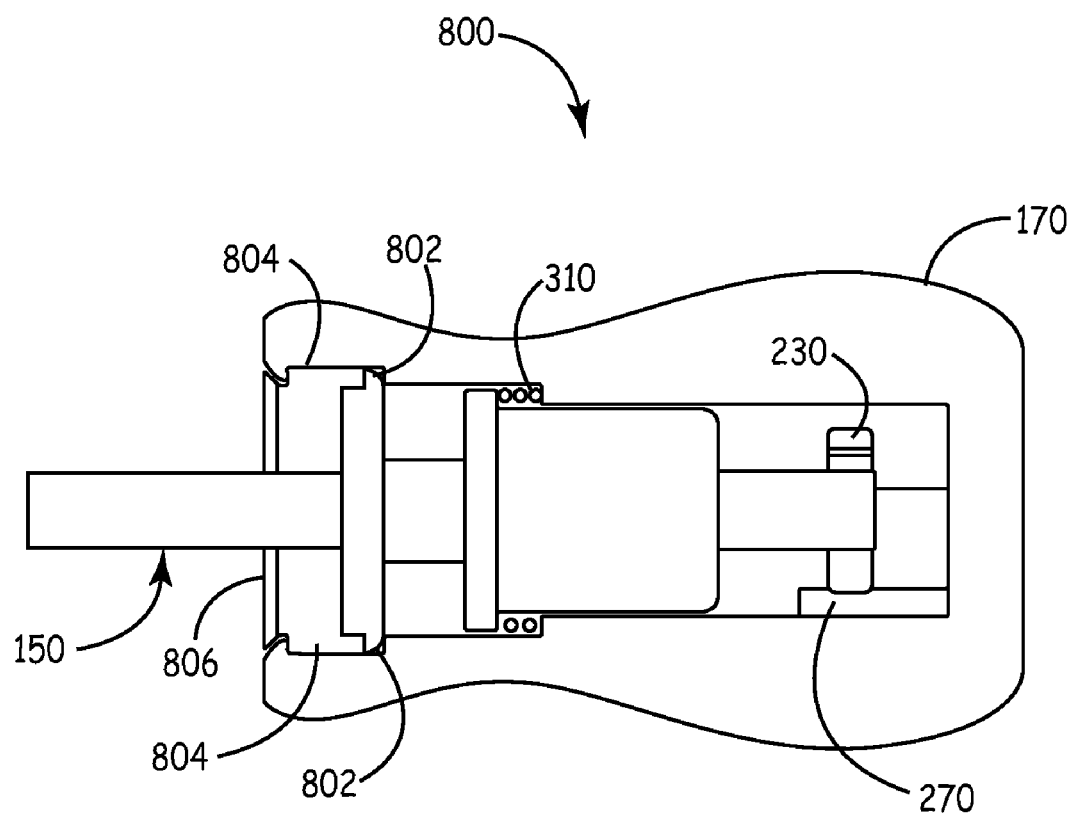
FIG. 32B is a schematic side view of the exemplary torque wrench of FIG. 31 in which a compression member is compressed around the drive shaft member.
Figure 33:
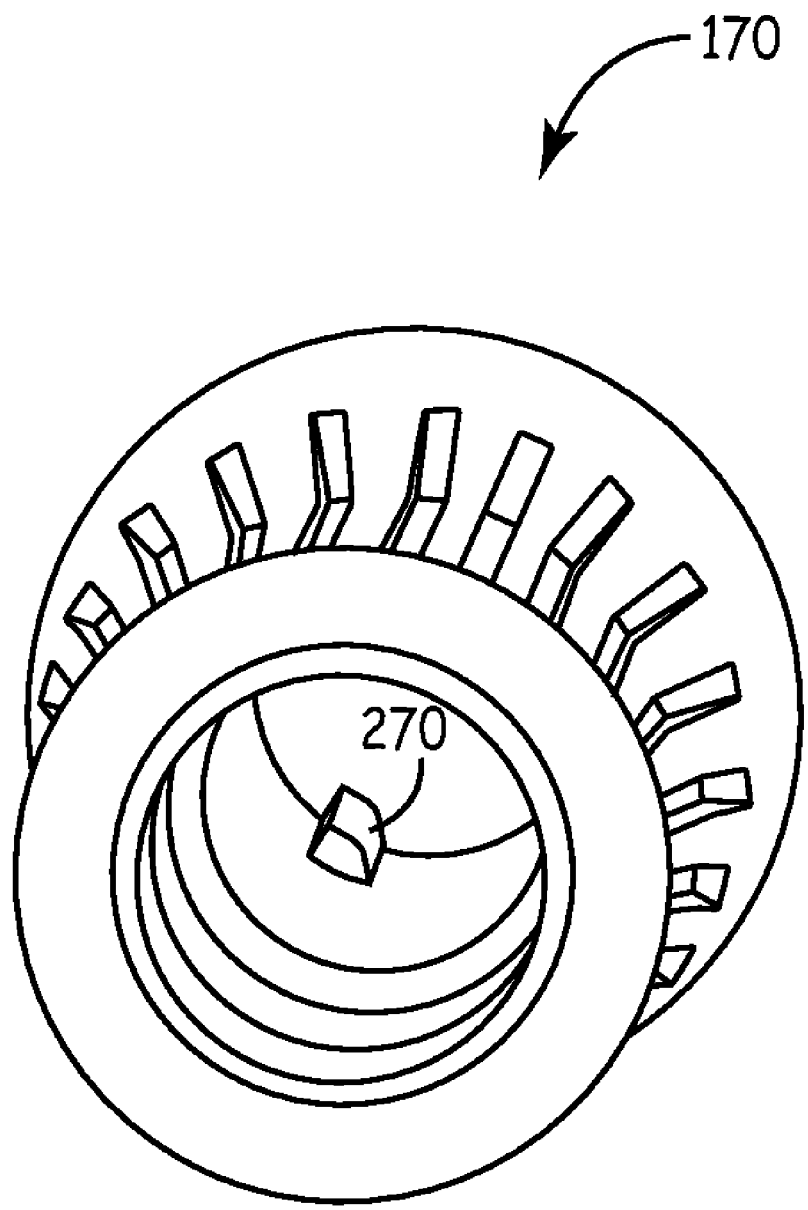
FIG. 33 is a schematic exterior view of an exemplary handle.
Figure 34:
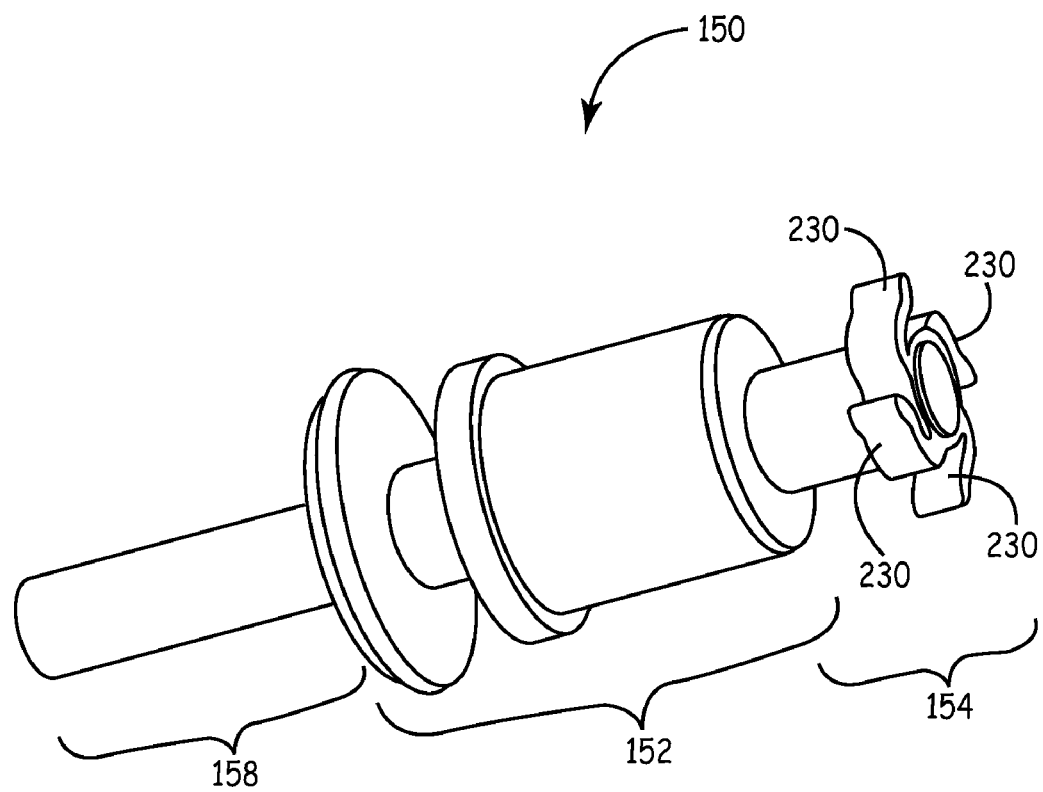
FIG. 34 is a schematic side view of an exemplary drive shaft member.
Figure 35:
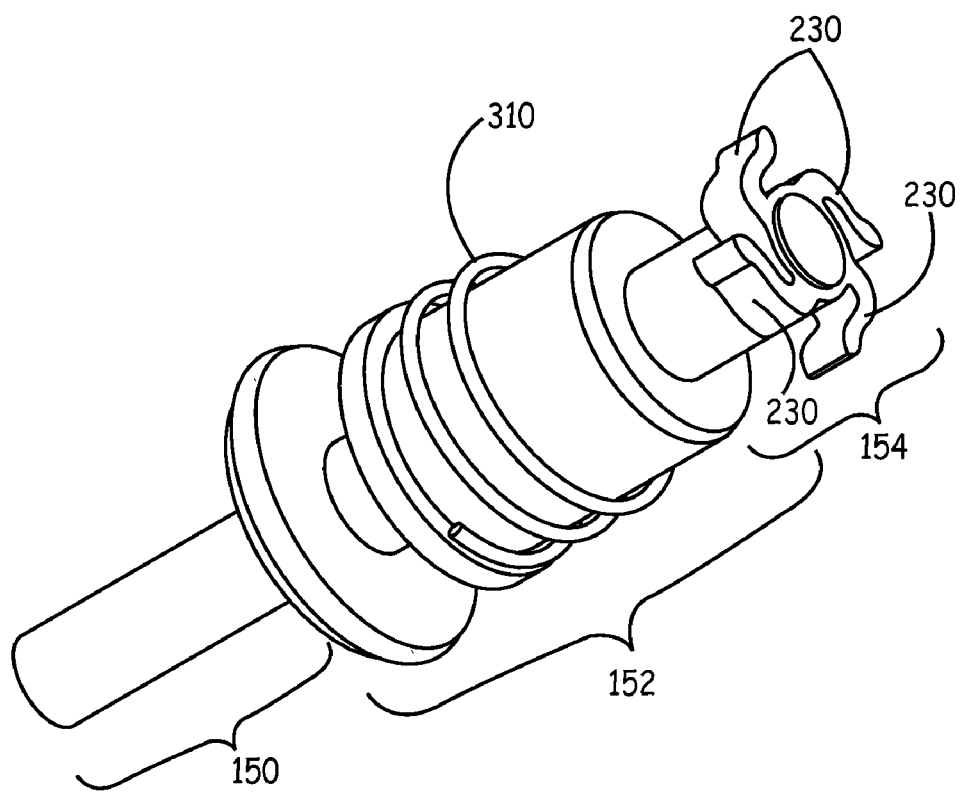
FIG. 35 is a schematic side view of an exemplary drive shaft member.

A second configuration occurs when handle 170 is being forced against an object. For example, a user can push the torque wrench 800 in the direction of the tool interface 220 against a connector 200, as shown in FIG. 2. As the user continues to push the torque wrench 800 against connector 200, the compressible member 310 is compressed or shortened along drive shaft axis 235, as shown in FIG. 32B. Compressing compressible member 800 locks or pushes together the handle 170 and the drive shaft member 150 along the drive shaft axis 235. Specifically, at least one or more fingers 230 are interlocked with anti-rotation members 270. The handle 150 is then unable to spin freely and can transfer significant torque to the drive shaft member 170. In this embodiment, no coupling body is used between the handle 170 and the drive shaft member 150. Instead, the flexible fingers 230 and the anti-rotation members serve as the interlocking features between the handle 170 and drive shaft member 150.

Figure 36:
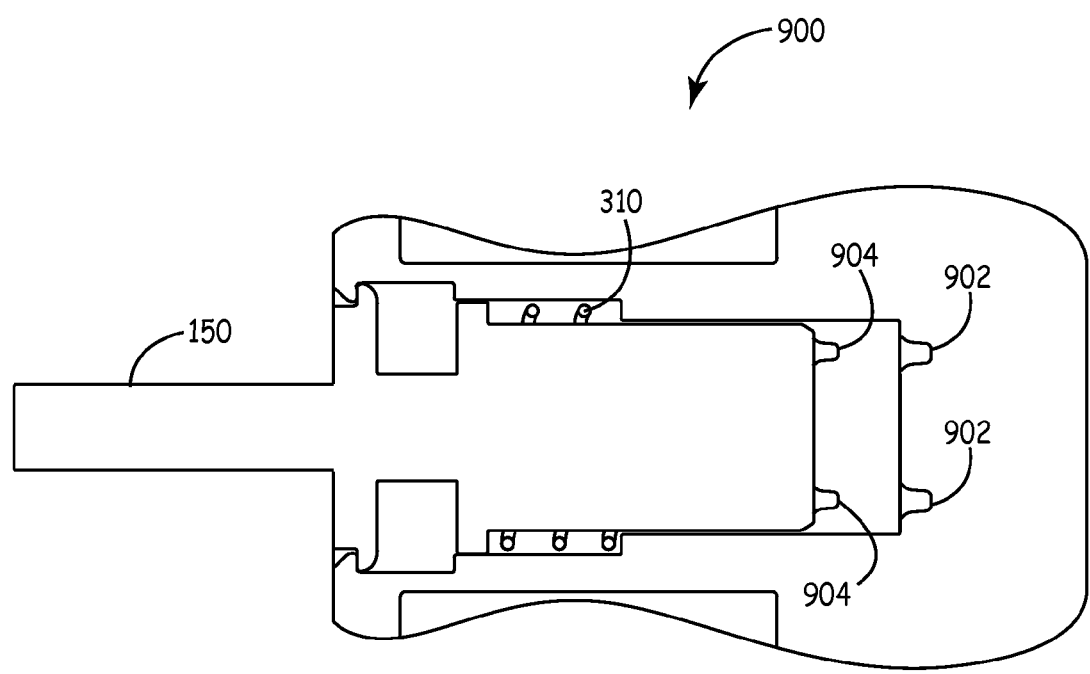
FIG. 36 is a schematic side view of yet another exemplary torque wrench.
Figure 37:
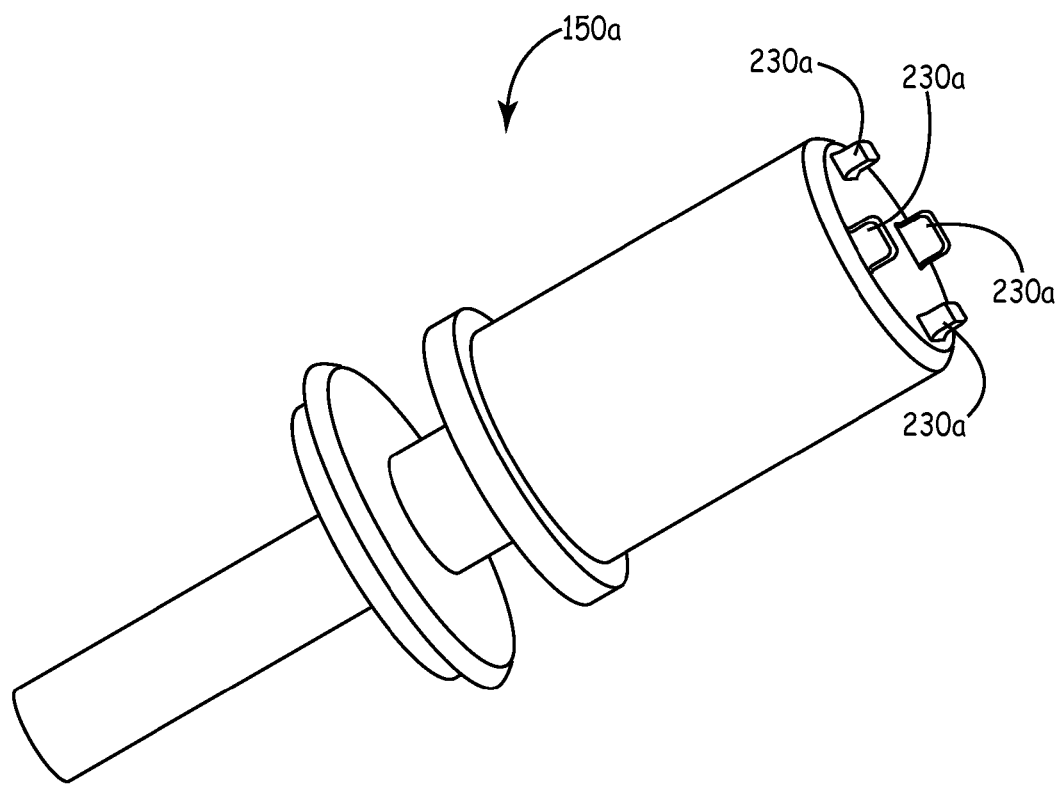
FIG. 37 is a schematic side view of an exemplary drive shaft member.
Figure 38:
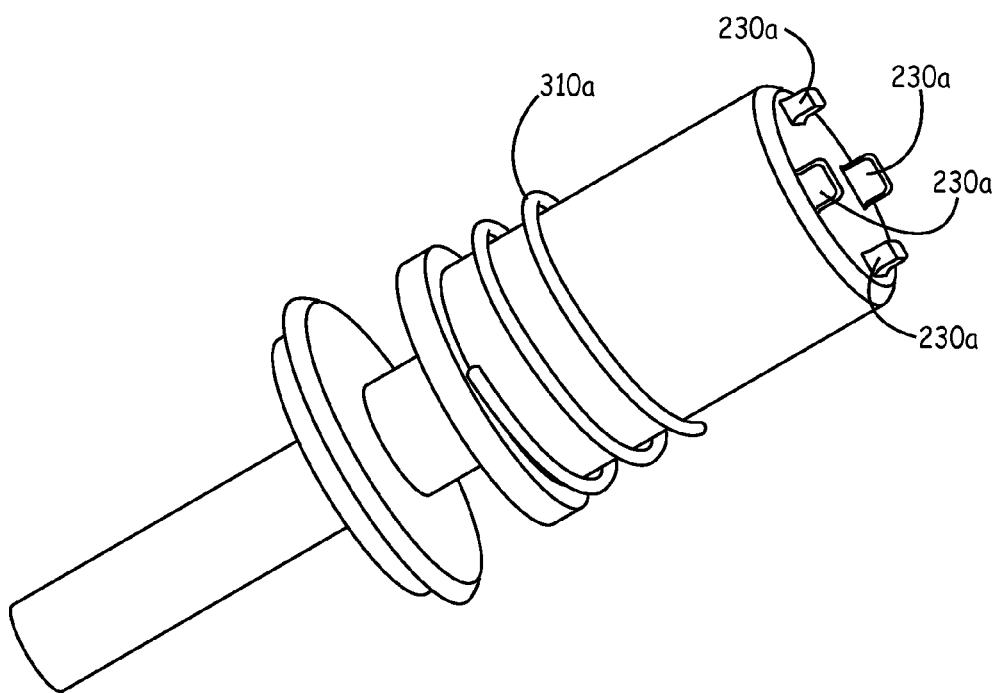
FIG. 38 is a schematic side view of an exemplary drive shaft member.

FIGS. 36-38 depict yet another embodiment of a torque wrench 900. Torque wrench 900 consists of, or, comprises a drive shaft member 150a, a handle 170, and a compressible member 310. In this embodiment, handle 170 includes protrusions 902 configured to mate with recessed areas 902 in drive shaft member 150a. In this embodiment, drive shaft member 150a is same as drive shaft member 150 except flexible members 230a are shaped as cylindrical members instead of as flexible fingers 230. Compressible member 310 can then be slid over a middle portion of handle 170 in order to move drive shaft member 150a from a relaxed position to an engagement position. Torque wrench 900 operates in a manner similar to torque wrenches previously described herein.

Although the present disclosure has been described in considerable detail with reference to certain disclosed embodiments, the disclosed embodiments are presented for purposes of illustration and not limitation and other embodiments of the disclosure are possible

What is claimed is:

1. An instrument comprising:
   a torque wrench for use with an implantable medical device, the torque wrench comprising:
   a handle having first and second ends and defining a bore extending between the first and second ends, the handle including a plurality of anti-rotation members extending from an inner surface into the bore at the second end of the handle;
   a drive shaft member including a middle portion having a first and second ends, a drive shaft extending from the first end and a plurality of fingers extending from an exterior surface that is located inside the handle, the plurality of fingers interdigitate with the anti-rotation members; and
   a compressible member surrounding a middle portion of the drive shaft member, the compressible member being movable between a first configuration in which the plurality of fingers are disengaged from the anti-rotation members and a second configuration in which the plurality of fingers are engaged to the anti-rotation members for transferring torque to the drive shaft.

2. The instrument of claim 1, wherein the compressible member is coupled along the radial axis of the middle portion of the drive shaft member.

3. The instrument of claim 1, wherein the plurality of fingers extend substantially perpendicular to a drive shaft axis.

4. The instrument of claim 1, wherein the drive shaft and the handle lack breakaway torque.

5. The instrument of claim 1, wherein the drive shaft forms a snap fit configuration with the handle.

6. The instrument of claim 2, wherein the compressible member is one of a helical spring, and a wave washer.

7. The instrument of claim 2, wherein the compressible member engages the plurality of fingers to the anti-rotation members when the drive shaft lacks engagement to a connector.

8. The instrument of claim 2, wherein each finger has a first portion, a second portion and a third portion.

9. The instrument of claim 8, wherein the second portion is a curve-shaped portion relative to the first portion.

10. The instrument of claim 1, wherein the fingers consist of a polymeric material.

11. An instrument comprising:
    a torque wrench for use with an implantable medical device, the torque wrench comprising:
    a handle having first and second ends and defining a bore extending between the first and second ends, the handle including a plurality of anti-rotation members extending from an inner surface into the bore at the second end of the handle;
    a drive shaft member including a middle portion having a first and second ends, a drive shaft extending from the first end and a plurality of fingers extending from an exterior surface that is located inside the handle, the plurality of fingers interdigitate with the anti-rotation members; and
    a compressible member surrounding a middle portion of the drive shaft member, the compressible member being movable between a first configuration in which the plurality of fingers are disengaged from the anti-rotation members and a second configuration in which the plurality of fingers are engaged to the anti-rotation members for transferring torque to the drive shaft;

wherein at least one finger has a first portion, a second portion and a third portion.

12. The instrument of claim 11, wherein the second portion is a curve-shaped portion relative to the first portion.

13. The instrument of claim 12, wherein the fingers consist of a polymeric material.

14. The instrument of claim 12, wherein an angle of less than 120° exists between the first and second portions.

15. The instrument of claim 12, wherein the second portion can move up to 150° relative to the first portion.

16. The instrument of claim 11, wherein the compressible member is one of a helical spring, and a wave washer.

* * * * *